US010039702B2

(12) United States Patent
Fujii et al.

(10) Patent No.: US 10,039,702 B2
(45) Date of Patent: Aug. 7, 2018

(54) CLEANSING COMPOSITION FOR SKIN OR HAIR

(71) Applicant: KAO CORPORATION, Tokyo (JP)

(72) Inventors: Ryosuke Fujii, Wakayama (JP); Yasuhiro Doi, Kainan (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/416,947

(22) PCT Filed: Sep. 19, 2013

(86) PCT No.: PCT/JP2013/076176
§ 371 (c)(1),
(2) Date: Jan. 23, 2015

(87) PCT Pub. No.: WO2014/046303
PCT Pub. Date: Mar. 27, 2014

(65) Prior Publication Data

US 2015/0182438 A1 Jul. 2, 2015

(30) Foreign Application Priority Data

Sep. 20, 2012 (JP) ................................ 2012-207638
Jun. 25, 2013 (JP) ................................ 2013-133195

(51) Int. Cl.

*A61K 8/46* (2006.01)
*A61Q 5/02* (2006.01)
*A61Q 19/10* (2006.01)
*A61K 8/73* (2006.01)
*A61K 8/44* (2006.01)
*A61Q 5/12* (2006.01)

(52) U.S. Cl.

CPC ................ *A61K 8/466* (2013.01); *A61K 8/44* (2013.01); *A61K 8/442* (2013.01); *A61K 8/46* (2013.01); *A61K 8/731* (2013.01); *A61K 8/732* (2013.01); *A61K 8/737* (2013.01); *A61Q 5/02* (2013.01); *A61Q 5/12* (2013.01); *A61Q 19/10* (2013.01); *A61K 2800/5424* (2013.01); *A61K 2800/5426* (2013.01); *A61K 2800/5428* (2013.01); *A61K 2800/596* (2013.01)

(58) Field of Classification Search

None
See application file for complete search history.

(56) References Cited

U.S. PATENT DOCUMENTS 3,332,878 A 7/1967 Coward et al.
3,708,437 A 1/1973 Sweeney
3,808,157 A 4/1974 Dewitt et al.
4,028,283 A 6/1977 Murata et al.
4,075,129 A 2/1978 Murata et al.
4,220,548 A 9/1980 Hashimoto et al.
4,507,223 A 3/1985 Tano et al.
4,555,351 A 11/1985 Morita et al.
4,589,988 A 5/1986 Rieck et al.
4,597,879 A 7/1986 Morita et al.
4,715,991 A 12/1987 Hirakouchi et al.
4,852,653 A 8/1989 Borchardt
4,925,976 A 5/1990 Terao et al.
5,078,916 A 1/1992 Kok et al.
5,580,494 A 12/1996 Sandhu et al.
5,876,705 A 3/1999 Uchiyama et al.
6,156,297 A 12/2000 Maurin et al.
6,184,190 B1 2/2001 D'Ambrogio et al.
6,403,654 B1 6/2002 De Oliveira
6,586,379 B1 7/2003 Seipel
6,656,454 B1 12/2003 Koester et al.
2002/0146442 A1 10/2002 Sendelbach et al.
2002/0193266 A1* 12/2002 Matsumoto .............. A61K 8/42 510/130
2007/0031362 A1 2/2007 Kreeger et al.
2011/0039744 A1 2/2011 Heath et al.
2012/0058067 A1 3/2012 Van Gogh et al.
2012/0270764 A1 10/2012 Brown et al.
2013/0252855 A1 9/2013 Weerasooriya et al.
2014/0079658 A1 3/2014 Terazaki et al.
2014/0080747 A1 3/2014 Hirahara et al.

(Continued)

FOREIGN PATENT DOCUMENTS

CA 1338239 C 4/1996
CN 88 1 02800 A 1/1987
EP 0 377 261 A2 7/1990

(Continued)

OTHER PUBLICATIONS

U.S. Office Action for U.S. Appl. No. 14/417,079, dated Jan. 25, 2016.
International Search Report and Written Opinion of the International Searching Authority dated Mar. 20, 2013, for International Application No. PCT/JP2013/076176.
International Search Report and Written Opinion of the International Searching Authority dated Mar. 20, 2014, for International Application No. PCT/JP2013/076171.
International Search Report and Written Opinion of the International Searching Authority dated Mar. 20, 2014, for International Application No. PCT/JP2013/076172.
International Search Report and Written Opinion of the International Searching Authority dated Mar. 20, 2014, for International Application No. PCT/JP2013/076173.

(Continued)

*Primary Examiner* — Ileana Popa
*Assistant Examiner* — Nicole P Babson
(74) *Attorney, Agent, or Firm* — Birch, Stewart, Kolasch & Birch, LLP

(57) ABSTRACT

Provided is a cleansing composition for skin or hair capable of bringing about a good rinse feel and durability of foam and, in regard to hair, imparting finger combability during rinsing as well as softness to hair during rinsing and after towel drying, and further, imparting a sufficient moist feeling also to skin after application. A cleansing composition for skin or hair, comprising the following (A) and (B): (A) an internal olefin sulfonate having 12 or more and 24 or less carbon atoms; and (B) a cationic polymer or an amphoteric polymer.

28 Claims, No Drawings

(56) References Cited

U.S. PATENT DOCUMENTS

| | | | |
|---|---|---|---|
| 2015/0202134 A1 | 7/2015 | Yoshikawa et al. | |

FOREIGN PATENT DOCUMENTS

| | | | |
|---|---|---|---|
| EP | 0351928 | B1 | 6/1993 |
| JP | 49-78706 | | 7/1974 |
| JP | 54-134711 | A | 10/1979 |
| JP | 55-43138 | A | 3/1980 |
| JP | 55-56196 | A | 4/1980 |
| JP | 56-167799 | A | 12/1981 |
| JP | 59-27995 | A | 2/1984 |
| JP | 59-222466 | A | 12/1984 |
| JP | 61-134366 | A | 6/1986 |
| JP | 1-151510 | A | 6/1989 |
| JP | 1-272564 | A | 10/1989 |
| JP | 2003-81935 | A | 3/2003 |
| JP | 2003-183152 | A | 7/2003 |
| JP | 2006-527785 | A | 12/2006 |
| JP | 2007-15940 | A | 1/2007 |
| JP | 2009-256211 | A | 11/2009 |

OTHER PUBLICATIONS

International Search Report and Written Opinion of the International Searching Authority dated Mar. 20, 2014, for International Application No. PCT/JP2013/076174.

Kosswig et al., "Surfactants", Wiley-VCH Verlag GmbH & Co. KGaA, Weinheim, 2005, XP002554753, pp. 1-76.

Kao Corporation, "KAO AKYPO RLM-45NV", Product Specification for Sodium Laureth-6 Carboxylate, retrieved online on Dec. 6, 2016, 1 page.

Wikihow, "How to Shampoo and Condition Your Hair," https://web.archive.org/web/20090418054258/http://www/wikihow.com/Shampoo-and-C . . . , Apr. 18, 2009, 2 pages.

Foster, "Sulfonation and Sulfation Processes," Chemithon, 1997, pp. 1-2.

Suresh et al., "Revisiting Markovnikov Addition to Alkenes via Molecular Electrostatic Potential," J. Org. Chem., vol. 66, No. 21, 2001 (published on web Sep. 18, 2001), pp. 6883-6890.

U.S. Office Action for U.S. Appl. No. 14/417,073, dated Aug. 24, 2017.

* cited by examiner

CLEANSING COMPOSITION FOR SKIN OR HAIR

FIELD OF THE INVENTION

The present invention relates to a cleansing composition for skin or hair such as a shampoo and a body shampoo.

BACKGROUND OF THE INVENTION

A cleansing agent is required to have a variety of functions such as emulsifying or cleaning the components of dirt and stains such as oil. Especially, unlike an industrial cleaner, a laundry cleaner, and a house cleaner, it is considered important that a cleansing agent used for skin or hair has not only detergency and excellent foaming performance, but also a favorable durability of foam, rinse feel and a good feel after rinsing and drying. Particularly in the case of hair, good finger combability and softness of the hair after rinsing and drying are desired, and in the case of skin, such an impression is desired that a moist feeling is imparted to the skin washed with a cleansing agent after drying.

Under the foregoing circumstances, olefin sulfonate, which is one of the anionic surfactants, is generally obtained by sulfonating olefin through reactions with a gaseous sulfur trioxide-containing gas, followed by neutralization and then hydrolysis of the resulting sulfonic acid. Olefin sulfonate is used in various cleansing agents.

For example, Patent Document 1 discloses a cleansing composition containing a specific internal olefin sulfonate for the purposes of increasing the solubilizing ability, penetrating ability, and interfacial tension reducing ability, and describes that when the above cleansing composition is used as a shampoo, it lathers well without friction, and achieves an improved feel. Also, Patent Document 2 discloses a cleansing composition containing a specific internal olefin sulfonate for the purposes of improving detergency, and describes examples of application to shampoos and the like, and Patent Document 3 also describes an aqueous liquid cleansing agent containing a specific internal olefin sulfonate and having a low cloud point.

Meanwhile, Patent Document 4 discloses a cellulose ether substituted with from 0.0003 to 0.08 moles, per mole of anhydroglucose unit, of a substituent containing an alkyl or arylalkyl group having from 8 to 24 carbon atoms and with a quaternary nitrogen-containing substituent, discloses a hair or skin care composition containing the above cellulose ether, and describes an improvement in the combability during wetting and drying, and a good wet and dry feel.

CITATION LIST

[Patent Document]

[Patent Document 1] JP-A-2003-81935

[Patent Document 2] U.S. Pat. No. 5,078,916

[Patent Document 3] U.S. Pat. No. 3,708,437

[Patent Document 4] JP-A-2006-527785

SUMMARY OF THE INVENTION

The present invention provides a cleansing agent for skin or hair, comprising the following (A) and (B) (hereinbelow, may also be referred to as "the cleansing composition of the present invention"):

(A) an internal olefin sulfonate having 12 or more and 24 or less carbon atoms; and (B) a cationic polymer or an amphoteric polymer.

Also, the present invention provides a method for washing hair, comprising applying the aforementioned cleansing composition of the present invention to hair, followed by washing and then rinsing (hereinbelow, may also be referred to as "the method for shampooing hair according to the present invention").

Further, the present invention provides a method for washing the body, comprising applying the aforementioned cleansing composition of the present invention to a surface of the skin, followed by washing and then rinsing (hereinbelow, may also be referred to as "the method for washing skin according to the present invention").

DETAILED DESCRIPTION OF THE INVENTION

A variety of polymers such as cationized guar gum and cationized hydroxyethyl cellulose are added to a cleansing agent for skin or hair in order to improve the feeling of the use of the product from the time of rinsing to after drying.

However, when those polymers are used in combination with existing anionic surfactants, sliminess may develop during rinsing and the durability of foam and rinse feel may be deteriorated, and softness of the hair during rinsing and after towel drying may be lost, and further, a moist feeling to the skin after drying tends to be insufficient. In view of the above, further improvement is sought for cleansing agents for skin or hair.

Accordingly, the present invention relates to a cleansing composition for skin or hair capable of bringing about a good durability of foam and rinse feel and, in regard to hair, imparting finger combability during rinsing as well as softness to hair during rinsing and after towel drying, and further, imparting a sufficient moist feeling also to skin after application.

In light of the above, the present inventors carried out various studies. As a result, they found that a cleansing composition which can impart softness to hair during rinsing and after towel drying and a sufficient moist feeling also to skin after application, while exhibiting an excellent durability of foam and rinse feel as a cleansing agent for skin or a cleansing agent for hair can be obtained by using a specific internal olefin sulfonate in combination with a specific polymer.

The cleansing composition of the present invention can not only bring about a good durability of foam and rinse feel, but also, when applied to hair, impart finger combability during rinsing, and softness to hair during rinsing and after towel drying, while when applied to skin, impart a good moist feeling to skin.

Hereinbelow, the present invention will be described in detail.

The cleansing composition of the present invention contains the following (A) and (B):

(A) an internal olefin sulfonate having 12 or more and 24 or less carbon atoms; and (B) a cationic polymer or an amphoteric polymer.

The reason is not clear why the cleansing composition of the present invention can impart not only a good durability of foam and rinse feel, but also softness to hair during rinsing and after towel drying, and a moist feeling to skin; it is presumed that because an internal olefin sulfonate having 12 or more and 24 or less carbon atoms has an adequate level of hydrophobicity, it strongly interacts with a cationic polymer or an amphoteric polymer, resulting in the production of a large amount of complexes formed between them, making their adsorption to skin and hair easy.

<Internal Olefin Sulfonate (A)>

From the viewpoint of environmental stability, low irritation, and the like, and also from the viewpoint of improving detergency, foam quality, and foamability, and a good durability of foam and rinse feel, and also, imparting to hair finger combability during rinsing, and softness during rinsing and after towel drying and a moist feeling to skin, the cleansing composition of the present invention contains an internal olefin sulfonate having 12 or more and 24 or less carbon atoms (hereinbelow, may also be referred to as a component (A)).

In the present invention, an internal olefin sulfonate is an olefin sulfonate obtained by sulfonating an internal olefin (an olefin having a double bond inside the olefin chain) as the raw material, followed by neutralization and then hydrolysis. It should be noted that the above internal olefin has a broad meaning including a trace amount of so-called α-olefin, in which a double bond is present at the C-1 position of the carbon chain. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). Here, the hydroxyl group of the hydroxyalkane sulfonate thus obtained is present inside the alkane chain, and the double bond of the olefin sulfonate is present inside the olefin chain. Also, the product thus obtained is mainly a mixture of the aforementioned substances, which may partially contain a trace amount of hydroxyalkane sulfonate having a hydroxyl group at the end of the carbon chain or olefin sulfonate having a double bond at the end of the carbon chain. In the present specification, each of these products and a mixture thereof are collectively referred to as internal olefin sulfonate (component (A)). It should be noted that hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

From the viewpoint of improving a durability of foam and rinse feel, and imparting to hair softness during rinsing and after towel drying, as well as good finger combability during rinsing and manageability after drying, a moist feeling to skin, the number of carbon atoms in the internal olefin sulfonate of the component (A) is 12 or more, preferably 14 or more, and more preferably 16 or more. Also, from the viewpoint of foamability, foam quality, softness of the hair during rinsing and after towel drying, and a moist feeling on the skin, the number of carbon atoms in the internal olefin sulfonate of the component (A) is 24 or less, preferably 20 or less, and more preferably 18 or less. Also, from the viewpoint of improving foamability, durability of foam and a rinse feel and imparting softness to hair during rinsing and after towel drying and a moist feeling to skin, the number of carbon atoms in the internal olefin sulfonate of the component (A) is 12 or more and 24 or less, preferably 14 or more and 20 or less, and more preferably 16 or more and 18 or less. These hydroxy form and olefin form containing various numbers of carbon atoms are derived from an internal olefin to be used as the raw material, and a hydroxy form and an olefin form containing different numbers of carbon atoms from those described above may also be contained.

From the viewpoint of improving detergency, foam quality, foamability, durability of foam and a rinse feel, and imparting to hair finger combability during rinsing, and softness during rinsing and after towel drying as well as a moist feeling to skin, the mass content ratio of an internal olefin sulfonate having 16 carbon atoms to an internal olefin sulfonate having 18 carbon atoms (internal olefin sulfonate having 16 carbon atoms/internal olefin sulfonate having 18 carbon atoms) in the component (A) or the cleansing composition of the present invention is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

It is to be noted that the aforementioned mass ratio may be measured by a high-performance liquid chromatograph-mass spectrometer (hereinbelow, abbreviated as HPLC-MS). Specifically, an internal olefin sulfonate having 16 carbon atoms and an internal olefin sulfonate having 18 carbon atoms are separated from the component (A) or the produced cleansing composition by HPLC, each of which may then be identified by analysis with MS, and from the HPLC-MS peak area of each internal olefin sulfonate, the mass ratio between them may be obtained.

From the viewpoint of improving detergency, foam quality, foamability, durability of foam and a rinse feel, and imparting to hair finger combability during rinsing, softness during rinsing and after towel drying as well as a moist feeling to skin, the total content of an internal olefin sulfonate having 16 carbon atoms and an internal olefin sulfonate having 18 carbon atoms in the component (A) is preferably 50% by mass or more, more preferably 60% by mass or more, more preferably 70% by mass or more, more preferably 80% by mass or more, more preferably 90% by mass or more, and even more preferably 95% by mass or more. It should be noted that the upper limit of the aforementioned total content is 100% by mass.

As is apparent from the aforementioned production method, the sulfonate group of the internal olefin sulfonate of the component (A) is present in the carbon chain of an internal olefin sulfonate, namely inside the olefin chain or alkane chain, and the component (A) may partially contain a trace amount of an internal olefin sulfonate having a sulfonate group at the end of the carbon chain. In the present invention, from the viewpoint of foamability, it is preferable that the content of an internal olefin sulfonate in which the sulfonate group is present at the C-2 position of the carbon chain is low, while the content of an internal olefin sulfonate in which the sulfonate group is present further inside is high in the component (A). It should be noted that when the component (A) contains an internal olefin sulfonate having 16 carbon atoms and an internal olefin sulfonate having 18 carbon atoms, it is more preferable that the content of an internal olefin sulfonate in which the sulfonate group is present at the C-2 position of the carbon chain is low, with respect to both of the above internal olefin sulfonates having 16 and 18 carbon atoms.

From the viewpoint of improving lathering property, foam quality, and a rinse feel as well as imparting finger combability during rinsing hair, softness to hair during rinsing and after towel drying and a moist feeling to skin, the content of an internal olefin sulfonate in which the sulfonate group is present at the C-2 position in the component (A) is preferably 25% by mass or less, more preferably 24% by mass or less, more preferably 23% by mass or less, more preferably 22% by mass or less, preferably 20% by mass or less, more preferably less than 20% by mass, more preferably 19% by mass or less, more preferably 18% by mass or less. Also, from the viewpoint of finger combability during rinsing, rinse feel, the content of an internal olefin sulfonate in which the sulfonate group is present at the C-2 position in the component (A) is preferably 17.5% by mass or less, more preferably 15% by mass or less, more preferably 12% by mass or less, and even more preferably 10% by mass or less. Also, from the viewpoint of reducing the production cost and improving productivity and from the viewpoint of durability of foam, softness during rinsing and after towel drying, the lower limit of the content of an internal olefin sulfonate in which the sulfonate group is present at the C-2 position in the component (A) is preferably 5% by mass or more, more preferably 6% by mass or more, more preferably 7% by mass or more, and even more preferably 8% by mass or more. Also, from the viewpoint of durability of foam, softness during rinsing, the lower limit of the content of an internal olefin sulfonate in which the sulfonate group is present at the C-2 position in the component (A) is preferably 9% by mass or more, more preferably 10% by mass or more, more preferably 12% by mass or more, more preferably 14% by mass or more, and even more preferably 16% by mass or more. Further, from the above viewpoints, the content of an internal olefin sulfonate in which the sulfonate group is present at the C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

Also, from the viewpoint of finger combability during rinsing, rinse feel, the content of an internal olefin sulfonate in which the sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less. Also, from the viewpoint of durability of foam, softness during rinsing and after towel drying, the content of an internal olefin sulfonate in which the sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

It should note that the content of an internal olefin sulfonate in which the sulfonate group is present at the C-2 position in the component (A) may be measured by a method such as nuclear magnetic resonance spectroscopy. More specifically, it may be measured by a method using gas chromatography described later in Example.

Also, from the viewpoint of improving lathering property, foam quality, durability of foam and a rinse feel as well as imparting to hair finger combability during rinsing, softness during rinsing and after towel drying and a moist feeling to skin, the content of an olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, durability of foam and a rinse feel as well as imparting to hair finger combability during rinsing, softness during rinsing and after towel drying as well as a moist feeling to skin, the content of an internal olefin sulfonate in which the sulfonate group is present further inside than the C-3 position of the olefin chain or alkane chain in the component (A) is preferably 70% by mass or more, more preferably 75% by mass or more, and even more preferably 80% by mass or more.

The internal olefin sulfonate is preferably a mixture of the hydroxy form and the olefin form. From the viewpoint of improving productivity and reducing impurities, the mass content ratio (hydroxy form/olefin form) of the hydroxy form of an internal olefin sulfonate to the olefin form of an internal olefin sulfonate in the component (A) or the cleansing composition is preferably from 50/50 to 100/0, more preferably from 60/40 to 100/0, more preferably from 70/30 to 100/0, more preferably from 75/25 to 100/0, and even more preferably from 75/25 to 95/5.

The mass content ratio of the hydroxy form of an internal olefin sulfonate to the olefin form of an internal olefin sulfonate in the component (A) or the cleansing composition of the present invention may be obtained by separating the hydroxy form and the olefin form from the component (A) or the produced cleansing composition by HPLC and then measuring the separated substances by the method described in Examples.

From the viewpoint of environmental stability, low irritation, and the like, and also from the viewpoint of improving a durability of foam and rinse feel as well as imparting finger combability during rinsing, softness during rinsing and after towel drying as well as a moist feeling to skin, the content of the aforementioned component (A) in the cleansing composition of the present invention is preferably 0.1% by mass or more, more preferably 1% by mass or more, more preferably 2% by mass or more, more preferably 5% by mass or more, more preferably 8% by mass or more, and even more preferably 10% by mass or more, from the viewpoint of improving manageability of hair after drying, finger combability during rinsing hair and rinse feel, the content of the aforementioned component (A) in the cleansing composition of the present invention is preferably 80% by mass or less, more preferably 50% by mass or less, more preferably 30% by mass or less, more preferably 20% by mass or less, and even more preferably 15% by mass or less. Also, from the viewpoint of above viewpoints, the content of the aforementioned component (A) in the cleansing composition of the present invention is preferably 0.1% by mass or more and 80% by mass or less, more preferably 1% by mass or more and 50% by mass or less, more preferably 2% by mass or more and 30% by mass or less, more preferably 5% by mass or more and 20% by mass or less, more preferably 8% by mass or more and 15% by mass or less, and even more preferably 10% by mass or more and 15% by mass or less.

The internal olefin sulfonate (A) is obtainable by sulfonating an internal olefin having 12 or more and 24 or less carbon atoms, followed by neutralization and then hydrolysis. No particular limitation is imposed on the conditions of sulfonation, neutralization, and hydrolysis, and for example, the conditions described in U.S. Pat. Nos. 1,633,184 and 2,625,150, and Tenside Surf. Det. 31 (5) 299 (1994) may be referred to.

As mentioned above, in the present invention, a raw material internal olefin refers to an olefin substantially having a double bond inside the olefin chain. From the viewpoint of improving the lathering property, durability of foam and rinse feel of the cleansing composition, imparting to hair finger combability during rinsing, softness during rinsing and after towel drying, as well as a moist feeling to skin, the number of carbon atoms in the internal olefin is preferably from 12 to 24, more preferably from 12 to 20, more preferably from 12 to 18, more preferably from 14 to 18, and even more preferably from 16 to 18. An internal olefin to be used as the raw material may be used singly or a combination of two or more thereof may be used.

From the viewpoint of acquiring lathering property and a creamy foam quality for easy washing, improving a rinse feel, imparting to hair finger combability during rinsing, softness during rinsing and after towel drying as well as a moist feeling to skin, a content of an internal olefin in which the double bond is present at the C-2 position in the raw material internal olefin is preferably 40% by mass or less, more preferably 35% by mass or less, more preferably 32% by mass or less, more preferably 30% by mass or less, more preferably 27% by mass or less, and also, from the viewpoint of finger combability during rinsing hair, rinse feel, more preferably 25% by mass or less, more preferably 20% by mass or less, more preferably less than 20% by mass, more preferably 19% by mass or less, and even more preferably 18% by mass or less. Also, from the viewpoint of reducing the production cost and improving productivity, and durability of foam, softness during rinsing, the lower limit of the aforementioned content is preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more, and also from the viewpoint of durability of foam, softness during rinsing, more preferably 20% by mass or more, more preferably 22% by mass or more, and even more preferably 24% by mass or more.

Also, from the above viewpoints, the content of an internal olefin in which the double bond is present at the C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

Further, from the viewpoint of finger combability during rinsing hair, rinse feel, a content of an internal olefin in which the double bond is present at the C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less. Also, from the viewpoint of durability of foam, softness during rinsing and after towel drying, a content of an internal olefin in which the double bond is present at the C-2 position in the raw material internal olefin is preferably 20% by mass or more and 27% by mass or less, more preferably 22% by mass or more and 27% by mass or less, and even more preferably 24% by mass or more and 27% by mass or less.

Also, from the viewpoint of improving lathering property, foam quality, durability of foam and rinse feel as well as imparting to hair finger combability during rinsing, softness during rinsing and after towel drying as well as a moist feeling to skin, the content of an olefin in which the double bond is present at the C-1 position, namely α-olefin, in the raw material internal olefin is preferably 3.0% by mass or less, more preferably 2.5% by mass or less, more preferably 2.0% by mass or less, more preferably 1.5% by mass or less, and even more preferably 1.0% by mass or less. From the viewpoint of reducing the production cost and improving productivity, the lower limit of the aforementioned content is preferably 0.01% by mass or more.

Further, from the viewpoint of improving lathering property, foam quality, and a rinse feel as well as imparting softness to hair during rinsing and after towel drying and a moist feeling to skin, the total content of a raw material internal olefin in which the double bond is present further inside than the C-3 position in the raw material internal olefin is preferably 65% by mass or more, more preferably 70% by mass or more, more preferably 75% by mass or more, and even more preferably 80% by mass or more.

The distribution of the double bond in the raw material internal olefin may be measured by a method described in Examples using a gas chromatograph mass spectrometer (hereinbelow, abbreviated as GC-MS). Specifically, components each having different carbon chain lengths and double bond positions are accurately separated by a gas chromatograph analyzer (hereinbelow, abbreviated as GC), and each component is then analyzed by a mass spectrometer (hereinbelow, abbreviated as MS) to identify the position of double bond in it, and from the resulting GC peak area, the fraction of each component may be found out.

The aforementioned sulfonation reaction may be carried out by reacting a sulfur trioxide gas with an internal olefin at a ratio of from 1.0 to 1.2 moles of sulfur trioxide per mole of the raw material internal olefin. The reactions are preferably carried out at a reaction temperature of from 20 to 40° C.

Neutralization is carried out by reacting from 1.0 to 1.5 times the molar amount of an alkali agent such as sodium hydroxide, ammonia, or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, and the like.

Also, in the production of the internal olefin sulfonate (A), the raw material internal olefin in which the number of carbon atoms is distributed in from 12 to 24 may be subjected to sulfonation, neutralization, and hydrolysis, or the raw material internal olefin having a uniform number of carbon atoms may be subjected to sulfonation, neutralization, and hydrolysis. Also, a plurality of internal olefin sulfonates each having different numbers of carbon atoms may be produced in advance and then mixed, as needed.

As the internal olefin sulfonate composition (A) of the present invention is obtained by sulfonating an internal olefin, followed by neutralization and hydrolysis as described above, an unreacted raw material internal olefin and inorganic compounds may remain in the composition (A). It is preferred that the contents of these components are much smaller.

The content of the raw material internal olefin in the component (A) of the present invention is preferably less than 5.0% by mass, more preferably less than 3.0% by mass, more preferably less than 1.5% by mass, and even more preferably less than 1.0% by mass in the component (A), from the viewpoint of improving durability of foam and rinse feel, and imparting to hair good finger combability and softness during rinsing and imparting moist feeling to skin.

The content of the unreacted internal olefin may be measured by a method described later in Examples.

The content of the inorganic compounds in the component (A) of the present invention is preferably less than 7.5% by mass, more preferably less than 5.0% by mass, more preferably less than 3.0% by mass, more preferably less than 2.0% by mass, and even more preferably less than 1.6% by mass in the component (A), from the viewpoint of improving durability of foam and rinse feel, and imparting to hair good finger combability and softness during rinsing and imparting moist feeling to skin.

In this context, the inorganic compounds include sulfates and alkali agents. The content of these inorganic compounds may be measured by a potentiometric titration. Specifically, the content may be measured by a method described later in Examples.

<Cationic Polymer or Amphoteric Polymer (B)>

From the viewpoint of improving a good durability of foam and rinse feel, imparting to hair finger combability during rinsing, as well as softness to hair during rinsing and after towel drying, and a moist feeling to skin after drying, the cleansing composition of the present invention contains a cationic polymer or an amphoteric polymer (hereinbelow, may also be referred to as a component (B)). Here, the cationic polymer refers to a polymer having a substituent which turns to a cation when dissolved in water, and the amphoteric polymer refers to a polymer having both a substituent which turns to a cation and a substituent which turns to an anion when dissolved in water, and this polymer combines the characteristics derived from both of these substituents.

From the viewpoint of imparting durability of foam, finger combability and softness during rinsing and softness after towel drying when the cleansing composition of the present invention is applied to hair, and also from the viewpoint of securing the volume of foam during washing and improving durability of foam and rinse feel and imparting a moist feeling after drying when the cleansing composition of the present invention is applied to the body, examples of a preferable cationic polymer to be used for the cleansing composition of the present invention include cationic galactomannan, cationized hydroxyethyl cellulose, cationized hydroxypropyl cellulose, cationized starch, or a synthetic polymer synthesized by a radical polymerization.

[Cationic Galactomannan]

The aforementioned cationic galactomannan is a polymer in which a cationic group is introduced into a galactomannan polysaccharide, and the cationic galactomannan is preferably a cationic polymer into which a quaternary nitrogen-containing substituent is introduced. The cationic galactomannan may be obtained by reacting a galactomannan polysaccharide with a cationizing agent.

From the viewpoint of enhancing the foaming performance by the cleansing composition and imparting durability of foam, finger combability and softness during rinsing and softness after towel drying when the cleansing composition of the present invention is applied to hair, and also from the viewpoint of securing the volume of foam during washing and improving durability of foam and rinse feel and imparting a moist feeling after drying when the cleansing composition of the present invention is applied to the body, examples of preferable cationic galactomannan to be used in the present invention include cationized tara gum, cationized locust bean gum, cationized Trigonella foenum-graecum gum, cationized guar gum, cationized cassia gum, cationized fenugreek gum, cationized honey locust gum, or cationized *Brachychiton acerifolium*. Among them, from the viewpoint of durability of foam during washing hair, finger combability and softness during rinsing, softness after towel drying, securing of the volume of foam during washing the skin, improving durability of foam and rinse feel, and imparting a moist feeling after drying brought about by the cleansing composition, cationized tara gum, cationized locust bean gum, cationized guar gum, cationized cassia gum, or cationized fenugreek gum are more preferable, of which cationized guar gum or cationized cassia gum is even more preferable.

Examples of a commercial product of the aforementioned cationized tara gum include CATINAL CTR-100 (the product of Toho Chemical Industry Co., Ltd.). Examples of a commercial product of the aforementioned cationized locust bean gum include CATINAL CLB-100 (the product of Toho Chemical Industry Co., Ltd.). Examples of a commercial product of the cationized Trigonella foenum-graecum gum include CATINAL CG-100 (the product of Toho Chemical Industry Co., Ltd.). Examples of a commercial product of the cationized guar gum include JAGUAR C-13S, JAGUAR C-14S, JAGUAR C-17, JAGUAR C-500, JAGUAR C-162, and JAGUAR EXCEL, all of which are sold by Rhodia, and N-Hance BF17, N-Hance 3215, N-Hance CCG450, N-Hance 3196, N-Hance BF13, N-Hance CG13, N-Hance CCG45, N-Hance 3000, AquaCat PF618, AquaCat CG518, and N-Hance HPCG1000, all of which are sold by Ashland Inc. Examples of a commercial product of the cationized cassia gum include Sensomer CT-250 polymer and Sensomer ST-400 polymer, both of which are sold by The Lubrizol Corporation.

[Cationized Hydroxyethyl Cellulose]

In the present invention, cationized hydroxyethyl cellulose (hereinbelow, may also be referred to as "C-HEC") refers to cellulose having a cationic group and an ethyleneoxy group. C-HEC is obtained by adding a cationic group and an ethyleneoxy group to cellulose. As the cationic group, a quaternary ammonium group is preferable.

Examples of a commercial product of C-HEC include UCARE JR125, UCARE JR400, UCARE JR30M, UCARE LR400, UCARE LR30M, SOFTCAT SL-5, SOFTCAT SL-30, SOFTCAT SL-60, SOFTCAT SL-100, SOFTCAT SX-400X, SOFTCAT SX-1300H, SOFTCAT SX-1300X, SOFTCAT SK-H, and SOFTCAT SK-MH, all of which are sold by The Dow Chemical Company.

[Cationized Hydroxypropyl Cellulose]

In the present invention, cationized hydroxypropyl cellulose (hereinbelow, may also be referred to as "C-HPC") refers to cellulose having a cationic group and a propyleneoxy group. The cationized hydroxypropyl cellulose is obtained by reacting a cationizing agent and propylene oxide with cellulose.

The cationized hydroxypropyl cellulose is preferably cationized hydroxypropyl cellulose having a main chain derived from anhydroglucose represented by the following general formula (1) and having a degree of substitution of the cationized ethyleneoxy group of from 0.01 to 2.9 and a degree of substitution of the propyleneoxy group of from 0.1 to 4.0 (hereinbelow, may also be referred to as "C-HPC").

(1)

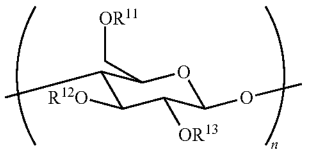

wherein $R^{11}$, $R^{12}$ and $R^{13}$ each independently represent a substituent having a cationized ethyleneoxy group and a propyleneoxy group represented by the following general formula (2) and n represents the average degree of polymerization of anhydroglucose, which is from 50 to 5000.

(2)

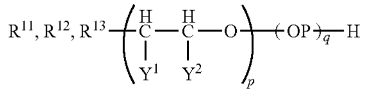

wherein one of $Y^1$ and $Y^2$ represents a hydrogen atom, and the other represents a cationic group represented by the following general formula (3), and PO represents a propyleneoxy group. The letter p represents the number of the cationized ethyleneoxy group (—CH($Y^1$)—CH($Y^2$)—O—), and q represents the number of the propyleneoxy group (—PO—) in the general formula (2), and each represents 0 or a positive integer. When neither p nor q is 0, the order of addition of the cationized ethyleneoxy group and propyleneoxy group does not matter, and further, when p and/or q is 2 or more, the moieties may be linked by either block bond or random bond.

(3)

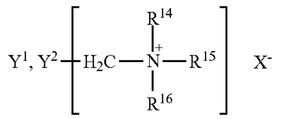

wherein $R^{14}$, $R^{15}$, and $R^{16}$ each independently represent a linear or branched alkyl group having 1 to 3 carbon atoms and $X^-$ represents an anionic group.

(Compound Represented by the General Formula (1))

$R^{11}$, $R^{12}$, and $R^{13}$ each independently represent a substituent represented by the general formula (2), and $R^{11}$, $R^{12}$, and $R^{13}$ may be the same or different.

(1)

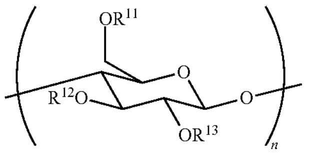

From the viewpoint of foaming performance, foam quality, rinse feel, durability of foam and finger combability of the hair during rinsing, the average degree of polymerization n in the general formula (1) is preferably 50 or more, more preferably 100 or more, more preferably 200 or more, and even more preferably 300 or more. Also, from the viewpoint of foaming performance, rinse feel, durability of foam and softness of the hair during rinsing, the average degree of polymerization n is 5000 or less, more preferably 3000 or less, more preferably 2000 or less, and even more preferably 1500 or less. Summing up the above viewpoints, the average degree of polymerization n in the general formula (1) is preferably from 50 to 5000, more preferably from 100 to 3000, more preferably from 200 to 2000, and even more preferably from 300 to 1500. It should be noted that the average degree of polymerization in the present invention refers to a viscosity-average degree of polymerization measured by the cuprammonium process, and specifically, it is calculated by the method described in Examples.

(Substituent Represented by the General Formula (2))

The substituent represented by the general formula (2) has, as shown in the following formula (2), a cationized ethyleneoxy group and a propyleneoxy group.

(2)

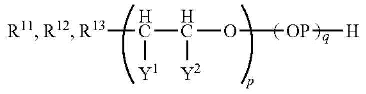

In the aforementioned general formula (2), one of $Y^1$ and $Y^2$ represents a hydrogen atom, and the other represents a cationic group represented by the following general formula (3), and PO represents a propyleneoxy group.

The letter p represents the number of the cationized ethyleneoxy group (—CH($Y^1$)—CH($Y^2$)—O—) contained in the general formula (2), and is 0 or a positive integer. From the viewpoint of easiness of production, p is preferably 0 or 1.

The letter q represents the number of the propyleneoxy group (—PO—), and is 0 or a positive integer. From the viewpoint of easiness of production, q is preferably an integer of from 0 to 4, more preferably an integer of from 0 to 2, and even more preferably 0 or 1.

When there is a plurality of substituents represented by the general formula (2) in the C-HPC molecule, the values of p and q may be different from each other among those substituents.

From the viewpoint of easiness of production, the sum of p and q is preferably an integer of from 1 to 5, more preferably an integer of from 1 to 4, more preferably an integer of from 1 to 3, and even more preferably 1 or 2. When neither p nor q is 0, the order of addition of the aforementioned cationized ethyleneoxy group and propyleneoxy group does not matter. Further, when neither p nor q is 0 and p and/or q is 2 or more, the moieties may be linked by either block bond or random bond; however, from the viewpoint of easiness of production, block bond is preferable.

(Cationic Group Represented by the General Formula (3))

The cationic group represented by the general formula (3) has a structure represented by the following formula.

(3)

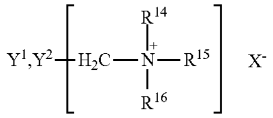

In the general formula (3), $R^{14}$, $R^{15}$, and $R^{16}$ each independently represent a linear or branched alkyl group having from 1 to 3 carbon atoms, and specific examples thereof include a methyl group, an ethyl group, an n-propyl group, or an isopropyl group. Among them, from the viewpoint of the water-solubility of C-HPC, a methyl group or an ethyl group is preferable, of which a methyl group is more preferable.

In the general formula (3), $X^-$ represents an anionic group, which is the counter ion of ammonium. No particular limitation is imposed on $X^-$ as long as it is an anionic group. Specific examples thereof include an alkyl sulfate ion, a sulfate ion, a phosphate ion, an alkyl carbonate ion, and a halide ion. Among them, from the viewpoint of easiness of production and availability, a halide ion is preferable.

Examples of the halide ion include a fluoride ion, a chloride ion, a bromide ion, and an iodide ion, and from the viewpoint of chemical stability, a chloride ion and a bromide ion are preferable, of which a chloride ion is more preferable.

In the C-HPC represented by the general formula (1), from the viewpoint of foaming performance, durability of foam, rinse feel, finger combability of the hair during rinsing, and softness, the degree of substitution of the cationized ethyleneoxy group is preferably 2.9 or less, more preferably 2.0 or less, more preferably 1.0 or less, and even more preferably 0.5 or less. Also, from the viewpoint of foaming performance, durability of foam, rinse feel, finger combability of the hair during rinsing, and softness, the degree of substitution of the cationized ethyleneoxy group is preferably 0.01 or more, more preferably 0.05 or more, and even more preferably 0.1 or more. Summing up the above viewpoints, the degree of substitution of the cationized ethyleneoxy group is preferably from 0.01 to 2.9, more preferably from 0.05 to 2.0, more preferably from 0.05 to 1.0, and even more preferably from 0.1 to 0.5.

In the present invention, the degree of substitution of the cationized ethyleneoxy group refers to an average number of moles of cationized ethyleneoxy group present in the C-HPC molecule per unit mole of the constituent anhydroglucose of the cellulose main chain. The degree of substitution of the cationized ethyleneoxy group is measured by the method described in Examples to follow.

In the C-HPC represented by the general formula (1), from the viewpoint of foaming performance, durability of foam, rinse feel, finger combability of the hair during rinsing, and softness, the degree of substitution of the propyleneoxy group is preferably 4.0 or less, more preferably 3.0 or less, more preferably 2.8 or less, and even more preferably 2.0 or less. Also, from the viewpoint of water-solubility, foaming performance, durability of foam, rinse feel, finger combability of the hair during rinsing, and softness, the degree of substitution of the propyleneoxy group is preferably 0.1 or more, more preferably 0.3 or more, more preferably 0.6 or more, and even more preferably 1.0 or more. Summing up the above viewpoints, the degree of substitution of the propyleneoxy group is preferably from 0.1 to 4, more preferably from 0.3 to 3.0, more preferably from 0.6 to 3.0, and even more preferably from 1.0 to 2.0.

In the present invention, the degree of substitution of the propyleneoxy group refers to an average number of moles of the propyleneoxy group present in the C-HPC molecule per unit mole of the constituent anhydroglucose of the cellulose main chain. The degree of substitution of the propyleneoxy group is measured by the method described in Examples to follow.

From the viewpoint of easiness of production, the sum of the degree of substitution of the cationized ethyleneoxy group and the degree of substitution of the propyleneoxy group is preferably 3.2 or less, more preferably 3.0 or less, more preferably 2.5 or less, and even more preferably 2.0 or less, and from the viewpoint of water-solubility, foaming performance, durability of foam, rinse feel, finger combability of the hair during rinsing, and softness, the aforementioned sum is preferably 0.9 or more, more preferably 1.2 or more, and even more preferably 1.5 or more. Summing up the above viewpoints, the sum of the degree of substitution of the cationized ethyleneoxy group and the degree of substitution of the propyleneoxy group is preferably from 0.9 to 3.2, more preferably from 1.2 to 3.0, more preferably from 1.2 to 2.5, and even more preferably from 1.2 to 2.0.

[Cationized Starch]

In the present invention, cationized starch refers to starch into which a quaternary nitrogen-containing substituent is introduced. The cationized starch is obtained by reacting a cationizing agent with starch. As a cationic group, a quaternary ammonium group is preferable. Examples of a commercial product of cationized starch include Sensomer CI-50, which is sold by The Lubrizol Corporation.

[Synthetic Polymer Synthesized by Radical Polymerization]

Examples of a preferable synthetic polymer to be used in the present invention include a methacryloxyalkyl quaternary ammonium salt/acrylamide copolymer, a diallyl quaternary ammonium salt/acrylamide copolymer, a diallyl quaternary ammonium salt/acrylic acid copolymer, a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, a diallyl quaternary ammonium salt/vinylpyrrolidone/vinylimidazole copolymer, or a cationic group-containing copolymer obtained by copolymerizing a monomer mixture containing the following monomers (a1), (a2), and (a3).

(Monomer (a1))

The monomer (a1) is at least one of the hydrophilic nonionic group-containing vinyl monomers represented by the general formula (4) or (5).

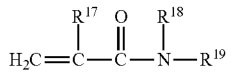

(4)

wherein, $R^{17}$ represents a hydrogen atom or a methyl group, $R^{18}$ represents a hydrogen atom, a linear or branched alkyl group or alkenyl group having from 1 to 4 carbon atoms, and $R^{18}$ represents a linear or branched alkyl group or alkenyl group having from 1 to 4 carbon atoms.

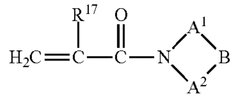

(5)

wherein, $R^{17}$ has the same meaning as above, $A^1$ and $A^2$ are the same or different and each represents a group represented by the formula $-(CH_2)n-$ (n is an integer of from 2 to 6), and B represents an $-O-$ or $-CH_2-$ group.

(Monomer (a2))

The monomer (a2) is at least one of the cationic group-containing vinyl monomers represented by the general formulas (6) and (7).

(6)

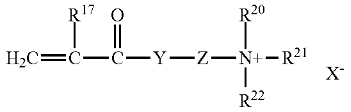

wherein, $R^{17}$ has the same meaning as above, $R^{20}$ and $R^{21}$ are the same or different and each represents an alkyl group or alkenyl group having from 1 to 4 carbon atoms, $R^{22}$ represents a hydrogen atom or an alkyl group having from 1 to 4 carbon atoms, Y represents an —O—, —NH—, —$CH_2$—, or —O—$CH_2CH(OH)$— group, Z represents a linear or branched alkylene group having from 1 to 4 carbon atoms (with the proviso that when Y is —$CH_2$—, Z has 0 to 3 carbon atoms), and $X^-$ represents a conjugated base of an acid.

(7)

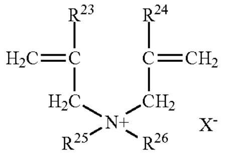

wherein, $R^{23}$ and $R^{24}$ are the same or different and each represents a hydrogen atom or a methyl group, $R^{25}$ and $R^{26}$ are the same or different and each represents a hydrogen atom or an alkyl group having from 1 to 4 carbon atoms, and $X^-$ has the same meaning as above.

(Monomer (a3))

Examples of the monomer (a3) include a crosslinkable monomer having two or more reactive unsaturated groups.

Among those monomers, from the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, they are more preferably a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, a diallyl quaternary ammonium salt/vinylpyrrolidone/vinylimidazole copolymer, or a cationic group-containing copolymer obtained by copolymerizing a monomer mixture containing (a1), (a2), and (a3).

Examples of a commercial product of the aforementioned methacryloxyalkyl quaternary ammonium salt/acrylamide copolymer include Merquat (trade mark) 5 (the product of The Lubrizol Corporation). Examples of a commercial product of the diallyl quaternary ammonium salt/acrylamide copolymer include Merquat (trade mark) 550, Merquat (trade mark) 740, Merquat (trade mark) 2200, and Merquat (trade mark) S (all are the products of The Lubrizol Corporation). Examples of a commercial product of the diallyl quaternary ammonium salt/acrylic acid copolymer include Merquat (trade mark) 280 and Merquat (trade mark) 295 (both are the products of The Lubrizol Corporation). Examples of a commercial product of the diallyl quaternary ammonium salt/acrylamide/acrylic acid copolymer include Merquat (trade mark) 3330 DRY (the product of The Lubrizol Corporation). Examples of a commercial product of the methacrylamide alkyl quaternary ammonium salt/acrylic acid/acrylic acid ester copolymer include Merquat (trade mark) 2001 (the product of The Lubrizol Corporation). Examples of a commercial product of the methacrylamide alkyl quaternary ammonium salt/acrylic acid/acrylamide copolymer include Merquat (trade mark) 2003 (the product of The Lubrizol Corporation). Examples of a commercial product of the diallyl quaternary ammonium salt/vinylpyrrolidone/vinyl imidazole copolymer include Luviquat (trade mark) Sensation, which is manufactured and sold by BASF. Examples of a commercial product of the cationic group-containing copolymer obtained by copolymerizing a monomer mixture containing (a1), (a2), and (a3) include SOFCARE KG-301W (the product of Kao Corporation) and SOFCARE KG-101W (the product of Kao Corporation).

From the viewpoint of enhancing the foaming performance by the cleansing composition and imparting durability of foam, finger combability and softness during rinsing, softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, examples of a preferable amphoteric polymer to be used in the cleansing composition of the present invention include a diallyl quaternary ammonium salt/acrylic acid copolymer, an acrylic acid/diallyl quaternary ammonium salt/acrylamide copolymer, or an acrylic acid/methacrylamidopropyl quaternary ammonium salt/alkyl acrylic acid ester copolymer.

From the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, the content of the aforementioned component (B) in the cleansing composition of the present invention is preferably 0.01% by mass or more, more preferably 0.02% by mass or more, more preferably 0.05% by mass or more, more preferably 0.1% by mass or more, and even more preferably 0.2% by mass or more. From the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel, imparting a moist feeling to the body after drying when the cleansing composition of the present invention is applied to the body, the content of the component (B) in the cleansing composition of the present invention is preferably 5% by mass or less, more preferably 1% by mass or less, and even more preferably 0.5% by mass or less. Further, from the above viewpoints, the content of the component (B) in the cleansing composition is preferably from 0.01 to 5% by mass, more preferably from 0.02 to 1% by mass, more preferably from 0.05 to 0.5% by mass, more preferably from 0.1 to 0.5% by mass, and even more preferably from 0.2 to 0.5% by mass.

From the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, the mass content ratio of the aforementioned component (A) to the aforementioned component (B), [Component (A)/Component (B)], is preferably from 5 to 250, more preferably from 10 to 100, and even more preferably from 20 to 50.

The cleansing composition of the present invention may contain a surfactant other than the aforementioned component (A) (hereinbelow, may also be referred to as a component (C)) so long as the effects of the present invention are not impaired.

As the surfactant other than the aforementioned component (A), any surfactant which is normally used in pharmaceutical products, quasi-drugs, cosmetics, toiletries, general merchandise, and the like may be used, and specific examples thereof include an anionic surfactant other than the aforementioned component (A), a nonionic surfactant, an amphoteric surfactant, and a cationic surfactant. Among them, from the viewpoint of improving the cleansing property, foamability, and foam quality, the surfactant other than the aforementioned component (A) is preferably an anionic surfactant other than the aforementioned component (A) or an amphoteric surfactant.

From the viewpoint of improving the cleansing property, foamability, and foam quality, the anionic surfactant other than the aforementioned component (A) is preferably a sulfuric acid ester salt, a sulfonic acid salt, a carboxylic acid salt, a phosphoric acid ester salt, and an amino acid salt. Specific examples thereof include a sulfuric acid ester salt such as alkyl sulfate, alkenyl sulfate, polyoxyalkylene alkyl ether sulfate, polyoxyalkylene alkenyl ether sulfate, and polyoxyalkylene alkyl phenyl ether sulfate; a sulfonic acid salt such as alkane sulfonate and acyl methyl taurate; a carboxylic acid salt such as a higher fatty acid salt having from 8 to 16 carbon atoms; a phosphoric acid ester salt such as alkyl phosphate and polyoxyalkylene alkyl ether phosphate; and an amino acid salt such as acyl glutamate, an alanine derivative, a glycine derivative, and an arginine derivative.

Also, from the viewpoint of cleansing property, foamability, and foam quality, the aforementioned anionic surfactant preferably has an alkyl group or alkenyl group having from 8 to 20 carbon atoms, and more preferably has an alkyl group or alkenyl group having from 10 to 16 carbon atoms.

Among such anionic surfactants, alkyl sulfate such as sodium lauryl sulfate, polyoxyethylene alkyl ether sulfate such as sodium polyoxyethylene lauryl ether sulfate, a higher fatty acid salt such as potassium laurate, acyl glutamate such as sodium N-acyl-L-glutamate, an acyl glycine salt, acyl methyl taurate, or alkyl phosphate is preferable, and sodium lauryl sulfate, ammonium polyoxyethylene (1) lauryl ether sulfate (ammonium laureth-1 sulfate), sodium polyoxyethylene (2) lauryl ether sulfate (sodium laureth-2 sulfate), potassium laurate, or sodium cocoyl glutamate is more preferable.

Examples of the aforementioned nonionic surfactant include a polyethylene glycol type nonionic surfactant such as polyoxyethylene sorbitan fatty acid ester, polyoxyethylene sorbitol fatty acid ester, polyoxyethylene glycerin fatty acid ester, polyoxyethylene fatty acid ester, polyoxyethylene alkyl ether, polyoxyethylene alkyl phenyl ether, and polyoxyalkylene (hydrogenated) castor oil, a polyhydric alcohol type nonionic surfactant such as sucrose fatty acid ester, polyglycerin alkyl ether, polyglycerin fatty acid ester, and alkyl glycoside, or fatty acid alkanolamide.

From the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, the nonionic surfactant preferably has, as the hydrophobic moiety, an alkyl group or alkenyl group having from 8 to 20 carbon atoms.

Among such nonionic surfactants, alkyl glycoside having from 8 to 18 carbon atoms, preferably from 8 to 12 carbon atoms such as decyl glucoside, polyoxyethylene alkyl ether such as polyoxyethylene lauryl ether, and fatty acid monoalkanolamide such as coconut oil fatty acid monoethanolamide are preferable, and decyl glucoside, polyoxyethylene (3) lauryl ether (laureth-3), polyoxyethylene (16) myristyl ether (ceteareth-16), coconut oil fatty acid monoethanolamide, or coconut oil fatty acid N-methyl monoethanolamide is more preferable.

Examples of the aforementioned amphoteric surfactant include a betaine surfactant such as imidazoline betaine, alkyldimethylaminoacetate betaine, fatty acid amidopropyl betaine or sulfobetaine, or an amine oxide surfactant such as alkyl dimethyl amine oxide.

Among such amphoteric surfactants, from the viewpoint of enhancing the foaming performance by the cleansing composition and imparting durability of foam, finger combability and softness during rinsing, and softness after towel drying when the cleansing composition of the present invention is applied to the hair, and also from the viewpoint of securing the volume of foam during washing and improving durability of foam and rinse feel and imparting a moist feeling to the body after drying when the cleansing composition of the present invention is applied to the body, imidazoline betaine, sulfobetaine, fatty acid amidopropyl betaine, and the like are preferable, and specifically, coconut oil fatty acid amidopropyl betaine, lauryl carbomethoxy methyl hydroxy imidazolium betaine, or lauryl hydroxy sulfobetaine is more preferable.

Examples of the aforementioned cationic surfactant include a mineral acid or organic acid salt of the tertiary amine represented by the following general formula (8) and a quaternary ammonium salt-type surfactant represented by the following general formula (9).

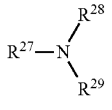

(8)

wherein, $R^{27}$ represents a linear or branched alkyl group or alkenyl group having from 6 to 28 carbon atoms which may be interrupted by an amide group, an ester group, or an ether group, and $R^{28}$ represents a linear or branched alkyl group, alkenyl group, or alkanol group having from 1 to 28 carbon atoms which may be interrupted by an amide group, an ester group, or an ether group, and $R^{29}$ represents a linear or branched alkyl group or alkanol group having from 1 to 3 carbon atoms.

In the general formula (8), from the viewpoint of securing durability of foam, volume of foam during washing the hair and imparting the finger combability and softness to hair during rinsing and softness to hair after towel drying when the cleansing composition of the present invention is applied to the hair, and also from the viewpoint of securing the volume of foam during washing the skin and improving durability of foam and rinse feel and imparting a moist feeling to the body after drying when the cleansing composition of the present invention is applied to the body, the number of carbon atoms in $R^{27}$ is preferably from 12 to 28, more preferably from 14 to 25, and even more preferably from 16 to 25. From a similar viewpoint, the number of carbon atoms in $R^{28}$ is preferably from 12 to 28, more preferably from 14 to 25, and even more preferably from 16 to 25, or $R^{28}$ is preferably a methyl group, an ethyl group, or a hydroxyethyl group. From a similar viewpoint, $R^{29}$ is preferably a methyl group, an ethyl group, or a hydroxyethyl group.

No particular limitation is imposed on the mineral acid or organic acid which forms a salt with the tertiary amine represented by the general formula (8); from the viewpoint of dispersion stability of a surfactant, hydrogen halide, sulfuric acid, acetic acid, citric acid, lactic acid, glutamic acid, and alkyl sulfate having from 1 to 3 carbon atoms are preferable, and from the viewpoint of chemical stability, hydrogen halide is preferably hydrogen chloride.

(9)

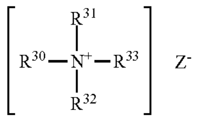

wherein, $R^{30}$ represents a linear or branched alkyl group or alkenyl group having from 6 to 28 carbon atoms which may be interrupted by an amide group, an ester group, or an ether group, $R^{31}$ represents a linear or branched alkyl group, alkenyl group, or alkanol group having from 1 to 28 carbon atoms which may be interrupted by an amide group, an ester group, or an ether group, and $R^{32}$ and $R^{33}$ each represent a linear or branched alkyl group having from 1 to 3 carbon atoms, and $Z^-$ represents an anionic group, which is the counter ion of an ammonium salt.

In the general formula (9), from the viewpoint of securing the volume of foam and durability of foam during washing the hair and imparting the finger combability and softness to hair during rinsing and softness to hair after towel drying when the cleansing composition of the present invention is applied to the hair, and also from the viewpoint of securing the volume of foam during washing the skin and improving durability of foam and rinse feel and imparting a moist feeling to the body after drying when the cleansing composition of the present invention is applied to the body, a preferred embodiment of $R^{30}$ is the same as a preferred embodiment of $R^{27}$ in the general formula (8). From a similar viewpoint, a preferred embodiment of $R^{31}$ is the same as a preferred embodiment of $R^{28}$ in the general formula (8). Also, from a similar viewpoint, $R^{32}$ and $R^{33}$ are each preferably a methyl group or an ethyl group.

No particular limitation is imposed on $Z^-$ as long as it is an anionic group. Specific examples thereof include an alkyl sulfate ion, a sulfate ion, a phosphate ion, alkyl carboxylate ion, or a halide ion. Among them, from the viewpoint of easiness of production and availability, a halide ion is preferable. Examples of the halide ion include a fluoride ion, a chloride ion, a bromide ion, or an iodide ion, and from the viewpoint of chemical stability, a chloride ion or a bromide ion is preferable, of which a chloride ion is more preferable.

Examples of the mineral acid or organic acid salt of the tertiary amine represented by the general formula (8) and the quaternary ammonium salt-type surfactant represented by the general formula (9) include mono long-chain alkyl trimethyl ammonium chloride, di long-chain alkyl dimethyl ammonium chloride, and a long-chain tertiary amine salt. Specific examples include mono long-chain alkyl trimethyl ammonium chloride such as stearyl trimethyl ammonium chloride, behenyl trimethyl ammonium chloride, cetyl trimethyl ammonium chloride, and stearoxy propyl trimethyl ammonium chloride; di long-chain alkyl dimethyl ammonium chloride such as distearyl dimethyl ammonium chloride and diisostearyl dimethyl ammonium chloride; mono long-chain dimethylamine such as stearyl dimethylamine, behenyl dimethylamine, octadecyloxypropyl dimethylamine, stearamidoethyl diethylamine, stearamidopropyl dimethylamine, and behenamidopropyl dimethylamine, a glutamic acid salt, a hydrochloric acid salt, a citric acid salt, or a lactic acid salt and the like of mono long-chain diethylamine. Among them, from the viewpoint of securing the volume of foam, durability of foam during washing the hair and imparting the finger combability and softness to hair during rinsing and softness to hair after towel drying when the cleansing composition of the present invention is applied to the hair, and also from the viewpoint of securing the volume of foam during washing the skin and improving durability of foam and rinse feel and imparting a moist feeling to the body after drying when the cleansing composition of the present invention is applied to the body, behenyl trimethyl ammonium chloride, cetyl trimethyl ammonium chloride, stearoxy propyl trimethyl ammonium chloride, stearyl dimethylamine, stearamidopropyl dimethylamine, or behenamidopropyl dimethylamine is preferable.

From the viewpoint of securing durability of foam, volume of foam during washing the hair and imparting the finger combability and softness to hair during rinsing and softness to hair after towel drying when the cleansing composition of the present invention is applied to the hair, and also from the viewpoint of securing the volume of foam during washing the skin and improving durability of foam and rinse feel and imparting a moist feeling to the body after drying when the cleansing composition of the present invention is applied to the body, the content of the aforementioned component (C) in the cleansing composition of the present invention is preferably 50% by mass or less, more preferably 30% by mass or less, more preferably 20% by mass or less, more preferably 15% by mass or less, more preferably 10% by mass or less, more preferably 5% by mass or less, and even more preferably 1% by mass or less. Also, from the viewpoint of improving the appearance, stability, lathering, and foam quality of the cleansing composition as well as the feel during rinsing and after drying, the content of the aforementioned component (C) in the cleansing composition of the present invention is preferably 0.5% by mass or more.

Also, from the viewpoint of securing volume of foam, durability of foam during washing the hair and imparting the finger combability and softness to hair during rinsing and softness to hair after towel drying when the cleansing composition of the present invention is applied to the hair, and also from the viewpoint of securing the volume of foam during washing the skin and improving durability of foam and rinse feel and imparting a moist feeling to the body after drying when the cleansing composition of the present invention is applied to the body, the mass content ratio of the aforementioned component (C) to the aforementioned component (A), [Component (C)/Component (A)], is preferably from 0 to 10, more preferably from 0 to 5, and even more preferably from 0 to 1.

The cleansing composition of the present invention may include an oil solution (hereinbelow, may also be referred to as a component (D)) so long as the effects of the present invention are not impaired.

As the oil solution, any one which is normally used in pharmaceutical products, quasi-drugs, cosmetics, toiletries, general merchandise, and the like may be used; from the viewpoint of further enhancing the finger combability of the hair during rinsing when the cleansing composition of the present invention is applied to the hair and imparting a moist feeling to the body after drying when the cleansing composition of the present invention is applied to the body, the oil solution is preferably one or more selected from an ester oil, a silicone oil, an ether oil, a hydrocarbon oil, a higher alcohol, and a carboxylic acid having a hydrocarbon group having from 17 to 23 carbon atoms which may be substituted by a hydroxyl group.

Specific examples of the aforementioned ester oil include castor oil, cacao oil, mink oil, avocado oil, olive oil, sunflower oil, *camellia* oil, apricot kernel oil, almond oil, wheat germ oil, *theobroma grandiflorum* seed oil, grape seed oil, babassu oil, jojoba oil, macadamia nut oil, *camellia* oleifera seed oil, shea butter oil, *camellia reticulata* seed oil, meadowfoam oil, bees wax, lanolin, hydrogenated lanolin, octyldodecyl lanolate, caprylyl eicosenoate, diisopropyl dimerate, myristyl 2-ethylhexanoate, cetyl 2-ethylhexanoate, stearyl 2-ethylhexanoate, octyl octanoate, lauryl octanoate, myristyl octanoate, isocetyl octanoate, octyl propylheptanoate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, propanediol dicaprate, diisopropyl adipate, diethoxyethyl succinate, 2-ethylhexyl succinate, sucrose polysoyate, sucrose polybehenate, sucrose tetraisostearate, glyceryl tribehenate, triisostearin, or pentaerythrityl tetrastearate.

Among them, from the viewpoint of further enhancing the finger combability of the hair during rinsing when the cleansing composition of the present invention is applied to the hair and imparting a moist feeling to the body after drying when the cleansing composition of the present invention is applied to the body, sunflower oil, avocado oil, *camellia* oil, macadamia nut oil, shea butter oil, octyl laurate, octyl myristate, octyldodecyl myristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate, or isotridecyl stearate is preferable, and one or more selected from sunflower oil, avocado oil, *camellia* oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate, and isostearyl isostearate are more preferable.

Also, as the aforementioned ester oil, a hydrophobic carboxylic acid ester of dipentaerythritol may also be used. The hydrophobic carboxylic acid ester of dipentaerythritol refers to a compound obtained by subjecting dipentaerythritol to dehydration condensation with one or more hydrophobic carboxylic acids. Here, the hydrophobic carboxylic acid refers to a carboxylic acid having a hydrocarbon group having from 16 to 24 carbon atoms optionally having a hydroxyl group. Specific examples of the hydrophobic carboxylic acid include palmitic acid, stearic acid, oleic acid, isostearic acid, hydroxystearic acid, and rosin acid. From the viewpoint of availability, an ester of mixed acid of hydroxystearic acid, stearic acid, and rosin acid and dipentaerythritol is preferable.

From the viewpoint of further enhancing the finger combability of the hair during rinsing when the cleansing composition of the present invention is applied to the hair and imparting a moist feeling to the body after drying when the cleansing composition of the present invention is applied to the body, as the aforementioned silicone oil, one or more selected from dimethylpolysiloxane, dimethiconol (dimethylpolysiloxane having a hydroxyl group at the end), and amino-modified silicone (dimethylpolysiloxane having an amino group within the molecule), polyether-modified silicone, glyceryl-modified silicone, amino derivative silicone, silicone wax, and silicone elastomer are preferable. From the viewpoint of the finger combability of the hair, a moist feeling to the skin after drying, and dispersibility during preparation of the cleansing composition of the present invention, the viscosity at 25° C. of the aforementioned silicone oil is preferably from 10 to 15,000,000 $mm^2/s$.

From the viewpoint of further enhancing the finger combability of the hair during rinsing when the cleansing composition of the present invention is applied to the hair and imparting a moist feeling to the body after drying when the cleansing composition of the present invention is applied to the body, examples of the aforementioned ether oil include polyoxypropylene hexyl ether, polyoxypropylene octyl ether, polyoxypropylene decyl ether, polyoxypropylene lauryl ether, dihexyl ether, dioctyl ether, didecyl ether, dilauryl ether, dimyristyl ether, dicetyl ether, distearyl ether, diicosyl ether, or dibehenyl ether in which the average number of moles of propyleneoxy groups added is from 1 to 15, preferably from 2 to 10. Among them, polyoxypropylene hexyl ether, polyoxypropylene octyl ether, polyoxypropylene decyl ether, polyoxypropylene lauryl ether, dioctyl ether, didecyl ether, and dilauryl ether in which the average number of moles of oxypropylene added is from 1 to 5, preferably from 2 to 4, and even more preferably 3 are preferable, and one or more selected from polyoxypropylene octyl ether, polyoxypropylene decyl ether, and polyoxypropylene lauryl ether in which the average number of moles of oxypropylene added is from 1 to 5, preferably from 2 to 4, and even more preferably 3 are more preferable.

From the viewpoint of further enhancing the finger combability of the hair during rinsing when the cleansing composition of the present invention is applied to the hair and imparting a moist feeling to the body after drying when the cleansing composition of the present invention is applied to the body, the aforementioned hydrocarbon oil is preferably saturated or unsaturated hydrocarbon having 20 or more carbon atoms.

Specific examples of the aforementioned hydrocarbon oil include squalene, squalane, liquid paraffin, liquid isoparaffin, heavy liquid isoparaffin, α-olefin oligomer, cycloparaffin, polybutene, petroleum jelly, paraffin wax, microcrystalline wax, polyethylene wax, or ceresin. From the viewpoint of further enhancing the finger combability of the hair during rinsing when the cleansing composition of the present invention is applied to the hair and imparting a moist feeling to the body after drying when the cleansing composition of the present invention is applied to the body, squalane, squalene, liquid paraffin, or paraffin wax is preferable, and one or more selected from squalane, liquid paraffin, and paraffin wax are more preferable.

From the viewpoint of further enhancing the finger combability of the hair during rinsing when the cleansing composition of the present invention is applied to the hair and imparting a moist feeling to the body after drying when the cleansing composition of the present invention is applied to the body, the aforementioned higher alcohol is preferably an alcohol having a linear or branched alkyl group or alkenyl group having from 6 to 22 carbon atoms. The number of carbon atoms in the above alkyl group or alkenyl group is more preferably from 8 to 20, and even more preferably from 12 to 18. Specific examples of the aforementioned higher alcohol include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, icosyl alcohol, or behenyl alcohol.

Among them, from the viewpoint of further enhancing the finger combability of the hair during rinsing when the cleansing composition of the present invention is applied to the hair and imparting a moist feeling to the body after drying when the cleansing composition of the present invention is applied to the body, lauryl alcohol, myristyl alcohol, cetyl alcohol, stearyl alcohol, behenyl alcohol, or 2-octyl dodecanol is preferable, of which lauryl alcohol, myristyl alcohol, cetyl alcohol, stearyl alcohol, or 2-octyl dodecanol is more preferable, and one or more selected from cetyl alcohol, stearyl alcohol, and 2-octyl dodecanol are more preferable.

The hydrocarbon group of the aforementioned carboxylic acid having a hydrocarbon group having from 17 to 23 carbon atoms which may be substituted by a hydroxyl group is preferably a linear or branched alkyl group or alkenyl group. Specific examples of the carboxylic acid having a hydrocarbon group having from 17 to 23 carbon atoms which may be substituted by a hydroxyl group include stearic acid, oleic acid, isostearic acid, hydroxystearic acid, behenic acid, or rosin acid. Among them, from the viewpoint of further enhancing the finger combability of the hair during rinsing when the cleansing composition of the present invention is applied to the hair and imparting a moist feeling to the body after drying when the cleansing composition of the present invention is applied to the body, stearic acid, oleic acid, isostearic acid, hydroxystearic acid, or behenic acid is preferable, of which oleic acid or isostearic acid is more preferable.

From the viewpoint of further enhancing the finger combability of the hair during rinsing when the cleansing composition of the present invention is applied to the hair and imparting a moist feeling to the body after drying when the cleansing composition of the present invention is applied to the body, the solubility of the aforementioned component (D) to be used in the present invention in 100 g of water at 20° C. is preferably from 0 to 1 g, more preferably from 0 to 0.5 g, and even more preferably from 0 to 0.1 g.

From the viewpoint of further enhancing the finger combability of the hair during rinsing when the cleansing composition of the present invention is applied to the hair and imparting a moist feeling to the body after drying when the cleansing composition of the present invention is applied to the body, the content of the aforementioned component (D) is preferably from 0.01 to 30% by mass, more preferably from 0.03 to 20% by mass, and even more preferably from 0.05 to 15% by mass. Also, from the viewpoint of further enhancing the finger combability of the hair during rinsing when the cleansing composition of the present invention is applied to the hair and imparting a moist feeling to the body after drying when the cleansing composition of the present invention is applied to the body, the mass content ratio of the aforementioned component (A) to the aforementioned component (D), [Component (A)/Component (D)], is preferably from 0.2 to 1000, more preferably from 0.5 to 200, more preferably from 1 to 100, and even more preferably from 5 to 50.

<Other Components>

The cleansing composition of the present invention may contain, in addition to the aforementioned components, water, which may serve as a medium in the production of the component (A), a viscosity reducing agent, polyhydric alcohols, a preservative, and a reducing agent, and also, other components used as ordinary cosmetic raw materials. Examples of such a component include a feel improver, a thickener, a fragrance, an ultraviolet absorber, a visible light absorber, a chelating agent, an antioxidant, a colorant, a preservative, a pH adjuster, a viscosity regulator, a pearlescent agent, and a moisturizing agent and the like.

<Production Method of the Cleansing Composition of the Present Invention>

No particular limitation is imposed on the production method of the cleansing composition of the present invention, and it may be produced by a conventional method. Specifically, for example, in the case of a liquid shampoo for hair, water, the aforementioned component (A), the aforementioned component (B), and if necessary, the aforementioned component (C) are heated and mixed to homogeneity. If necessary, the aforementioned component (A) may be dispersed or dissolved in water in advance, and then added. The cleansing composition of the present invention may also be prepared by adding the aforementioned component (A) to an aqueous solution of a surfactant and homogeneously dissolving or dispersing it, followed by cooling, and if necessary, adding a pearlescent agent, a pH adjuster, a fragrance, a dye, and the like.

No particular limitation is imposed on the form of the cleansing composition of the present invention, and it may be provided in any form such as a liquid, a foam, a paste, a cream, a solid, and a powder, among which a liquid, a paste, or a cream is preferable, and a liquid is more preferable. When the cleansing composition is provided as a liquid, polyethylene glycol, ethanol, and the like are preferably used as a liquid medium in addition to water. The content of water in the cleansing composition of the present invention is preferably 10% by mass or more and 95% by mass or less.

<Intended Use and Method of Use>

The cleansing composition of the present invention may impart not only a good durability of foam and rinse feel, finger combability during rinsing, as well as softness to hair during rinsing and after towel drying, but also a moist feeling to skin after drying; therefore, it can be preferably used as a cleansing composition for hair or a cleansing composition for skin. Examples of the cleansing composition for hair include a hair shampoo. Examples of the cleansing composition for skin include a body shampoo, a face wash, a makeup remover, or a hand soap.

Because the cleansing composition of the present invention can impart not only a good durability of foam and rinse feel, finger combability during rinsing, as well as softness to hair during rinsing and after towel drying, but also a moist feeling to skin after drying, a method for washing the hair which includes applying the aforementioned cleansing composition of the present invention to hair, followed by washing and then rinsing is also provided. Also, a method for washing the body which includes applying the aforementioned cleansing composition of the present invention to a surface of the skin, followed by washing and then rinsing is also provided.

Pertaining to the aforementioned embodiments, the present invention further discloses the following cleansing composition for skin or hair and a method for washing the hair and a method for washing the body using the above cleansing composition for skin or hair.

[1] A cleansing composition for skin or hair, comprising the following (A) and (B):

(A) an internal olefin sulfonate having 12 or more and 24 or less carbon atoms; and (B) a cationic polymer or an amphoteric polymer.

[2] The cleansing composition for skin or hair according to the aforementioned [1], wherein the number of carbon atoms in the internal olefin sulfonate is preferably 14 or more, more preferably 16 or more, and is preferably 20 or less, and preferably 18 or less.

[3] The cleansing composition for skin or hair according to the aforementioned [1] or [2], wherein the mass content ratio of an internal olefin sulfonate having 16 carbon atoms to an internal olefin sulfonate having 18 carbon atoms (internal olefin sulfonate having 16 carbon atoms/internal olefin sulfonate having 18 carbon atoms) in the component (A) is preferably from 50/50 to 99/1, more preferably from 60/40 to 95/5, more preferably from 70/30 to 90/10, more preferably from 75/25 to 90/10, more preferably from 75/25 to 85/15, and even more preferably from 78/22 to 85/15.

[4] The cleansing composition for skin or hair according to any one of the aforementioned [1] to [3], wherein the total content of an internal olefin sulfonate having 16 carbon atoms and an internal olefin sulfonate having 18 carbon atoms in the component (A) is preferably 50% by mass or more, more preferably 60% by mass or more, more preferably 70% by mass or more, more preferably 80% by mass or more, more preferably 90% by mass or more, and even more preferably 95% by mass or more.

[5] The cleansing composition for skin or hair according to any one of the aforementioned [1] to [4], wherein a content of an internal olefin sulfonate in which a sulfonate group is present at a C-2 position in the component (A) is preferably 25% by mass or less, more preferably 24% by mass or less, more preferably 23% by mass or less, more preferably 22% by mass or less; more preferably 20% by mass or less, more preferably less than 20% by mass, more preferably 19% by mass or less, and even more preferably 18% by mass or more.

[6] The cleansing composition for skin or hair according to any one of the aforementioned [1] to [5], wherein a content of an internal olefin sulfonate in which a sulfonate group is present at a C-2 position in the component (A) is preferably 5% by mass or more and 25% by mass or less, more preferably 5% by mass or more and 24% by mass or less, more preferably 5% by mass or more and 23% by mass or less, more preferably 5% by mass or more and 22% by mass or less, preferably 5% by mass or more and 20% by mass or less, more preferably 6% by mass or more and less than 20% by mass, more preferably 7% by mass or more and 19% by mass or less, and even more preferably 8% by mass or more and 18% by mass or less.

[7] The cleansing composition for skin or hair according to any one of the aforementioned [1] to [6], wherein a content of the internal olefin sulfonate in which a sulfonate group is present at the C-2 position in the component (A) is preferably 9% by mass or more and 17.5% by mass or less, more preferably 9% by mass or more and 15% by mass or less, more preferably 9% by mass or more and 12% by mass or less, and even more preferably 9% by mass or more and 10% by mass or less.

[8] The cleansing composition for skin or hair according to any one of the aforementioned [1] to [7], wherein a content of the internal olefin sulfonate in which a sulfonate group is present at the C-2 position in the component (A) is preferably 9% by mass or more and 18% by mass or less, more preferably 10% by mass or more and 18% by mass or less, more preferably 12% by mass or more and 18% by mass or less, more preferably 14% by mass or more and 18% by mass or less, and even more preferably 16% by mass or more and 18% by mass or less.

[9] The cleansing composition for skin or hair according to any one of the aforementioned [1] to [8], wherein a content of an internal olefin sulfonate in which a sulfonate group is present at a C-2 position in the component (A) is preferably 5% by mass or more, more preferably 6% by mass or more, more preferably 7% by mass or more, more preferably 8% by mass or more, more preferably 9% by mass or more, more preferably 10% by mass or more, more preferably 12% by mass or more, more preferably 14% by mass or more, and even more preferably 16% by mass or more.

[10] The cleansing composition for skin or hair according to any one of the aforementioned [1] to [9], wherein the content of an internal olefin sulfonate in which the sulfonate group is present at the C-2 position in the component (A) is preferably 20% by mass or less, more preferably less than 20% by mass, more preferably 19% by mass or less, more preferably less than 18% by mass, more preferably 17.5% by mass or less, and is preferably 5% by mass or more, more preferably 6% by mass or more, more preferably 7% by mass or more, more preferably 8% by mass or more, and even more preferably 9% by mass or more.

[11] The cleansing composition for skin or hair according to any one of the aforementioned [1] to [10], wherein the content of an internal olefin sulfonate in which the sulfonate group is present at the C-1 position of the olefin chain or alkane chain in the component (A) is preferably 3.0% by mass or less, more preferably 2.5% by mass or less, more preferably 2.0% by mass or less, more preferably 1.5% by mass or less, more preferably 1.0% by mass or less, and preferably 0.01% by mass or more.

[12] The cleansing composition for skin or hair according to any one of the aforementioned [1] to [11], wherein the mass content ratio (hydroxy form/olefin form) of the hydroxy form of an internal olefin sulfonate to the olefin form of an internal olefin sulfonate in the component (A) is preferably from 50/50 to 100/0, more preferably from 60/40 to 100/0, more preferably from 70/30 to 100/0, more preferably from 75/25 to 100/0, and even more preferably from 75/25 to 95/5.

[13] The cleansing composition for skin or hair according to any one of the aforementioned [1] to [12], wherein when the component (A) is obtained by a sulfonation of a raw material internal olefin, followed by neutralization and then hydrolysis, the content of an internal olefin in which the double bond is present at a C-2 position in the raw material internal olefin is preferably 40% by mass or less, more preferably 35% by mass or less, more preferably 32% by mass or less, and even more preferably 30% by mass or less, and preferably 5% by mass or more, more preferably 6% by mass or more, more preferably 7% by mass or more, more preferably 8% by mass or more, more preferably 9% by mass or more, more preferably 12% by mass or more, and even more preferably 15% by mass or more.

[14] The cleansing composition for skin or hair according to any one of the aforementioned [1] to [13], wherein when the component (A) is obtained by a sulfonation of the raw material internal olefin, followed by neutralization and then hydrolysis, a content of the internal olefin in which the double bond is present at a C-2 position in the raw material internal olefin is preferably 5% by mass or more and 40% by mass or less, more preferably 5% by mass or more and 35% by mass or less, more preferably 5% by mass or more and 32% by mass or less, more preferably 5% by mass or more and 30% by mass or less, preferably 6% by mass or more and 30% by mass or less, more preferably 7% by mass or more and 30% by mass or less, more preferably 8% by mass or more and 30% by mass or less, more preferably 9% by mass or more and 30% by mass or less, more preferably 12% by mass or more and 30% by mass or less, and even more preferably 15% by mass or more and 27% by mass or less.

[15] The cleansing composition for skin or hair according to any one of the aforementioned [1] to [14], wherein when the component (A) is obtained by a sulfonation of the raw material internal olefin, followed by neutralization and then hydrolysis, a content of the internal olefin in which the double bond is present at a C-2 position in the raw material internal olefin is preferably 15% by mass or more and 25% by mass or less, more preferably 15% by mass or more and 20% by mass or less, more preferably 15% by mass or more and less than 20% by mass, more preferably 15% by mass or more and 19% by mass or less, and even more preferably 15% by mass or more and 18% by mass or less.

[16] The cleansing composition for skin or hair according to any one of the aforementioned [1] to [15], wherein when the component (A) is obtained by a sulfonation of the raw material internal olefin, followed by neutralization and then hydrolysis, a content of the internal olefin in which the double bond is present at a C-2 position in the raw material internal olefin is preferably 20% by mass or more and 27% by mass or less, more preferably 22% by mass or more and 27% by mass or less, and even more preferably 24% by mass or more and 27% by mass or less.

[17] The cleansing composition for skin or hair according to any one of the aforementioned [1] to [16], wherein the content of the component (A) is preferably 0.1% by mass or more, more preferably 1% by mass or more, more preferably 2% by mass or more, even more preferably 5% by mass or more, more preferably 8% by mass or more, and even more preferably 10% by mass or more, and is preferably 80% by mass or less, more preferably 50% by mass or less, more preferably 30% by mass or less, more preferably 20% by mass or less, and even more preferably 15% by mass or less.

[18] The cleansing composition for skin or hair according to any one of the aforementioned [1] to [17], wherein a content of the raw material internal olefin in the component (A) is preferably less than 5.0% by mass, more preferably less than 3.0% by mass, more preferably less than 1.5% by mass, and even more preferably less than 1.0% by mass in the component (A).

[19] The cleansing composition for skin or hair according to any one of the aforementioned [1] to [18], wherein a content of the inorganic compounds in the component (A) is preferably less than 7.5% by mass, more preferably less than 5.0% by mass, more preferably less than 3.0% by mass, more preferably less than 2.0% by mass, and even more preferably less than 1.6% by mass in the component (A).

[20] The cleansing composition for skin or hair according to any one of the aforementioned [1] to [19], wherein the cationic polymer is preferably one or two or more selected from cationic galactomannan, cationized hydroxyethyl cellulose, cationized hydroxypropyl cellulose, cationized starch, and a synthetic polymer synthesized by a radical polymerization.

[21] The cleansing composition for skin or hair according to any one of the aforementioned [1] to [20], wherein the content of the component (B) is preferably 0.01% by mass or more, more preferably 0.02% by mass or more, more preferably 0.05% by mass or more, more preferably 0.1% by mass or more, and even more preferably 0.2% by mass or more, and is preferably 5% by mass or less, more preferably 1% by mass or less, and more preferably 0.5% by mass or less.

[22] The cleansing composition for skin or hair according to any one of the aforementioned [1] to [21], wherein the mass content ratio of the component (A) to the component (B), [Component (A)/Component (B)], is preferably from 5 to 250, more preferably from 10 to 100, and more preferably from 20 to 50.

[23] The cleansing composition for skin or hair according to any one of the aforementioned [1] to [22], further comprising a surfactant (C) other than the component (A).

[24] The cleansing composition for skin or hair according to the aforementioned [23], wherein the component (C) is preferably an anionic surfactant or an amphoteric surfactant other than the component (A).

[25] The cleansing composition for skin or hair according to the aforementioned [23] or [24], wherein the surfactant other than the component (A) is preferably one or two or more selected from a sulfuric acid ester salt, a sulfonic acid salt, a carboxylic acid salt, a phosphoric acid ester salt, and an amino acid salt.

[26] The cleansing composition for skin or hair according to any one of the aforementioned [23] to [25], wherein the content of the component (C) is preferably 50% by mass or less, more preferably 30% by mass or less, more preferably 20% by mass or less, more preferably 15% by mass or less, more preferably 10% by mass or less, more preferably 5% by mass or less, and even more preferably 1% by mass or less, and is preferably 0.5% by mass or more, more preferably 1% by mass or more, and even more preferably 2% by mass or more.

[27] The cleansing composition for skin or hair according to any one of the aforementioned [23] to [26], wherein the mass content ratio of the component (A) and the component (C), [Component (C)/Component (A)], is preferably from 0 to 10, more preferably from 0 to 5, and even more preferably from 0 to 1.

[28] A method for washing the hair, comprising applying the cleansing composition for skin or hair according to any one of the aforementioned [1] to [27] to hair, followed by washing and then rinsing.

[29] A method for washing the body, comprising applying the cleansing composition for skin or hair according to any one of the aforementioned [1] to [27] to a surface of the skin, followed by washing and then rinsing.

[30] A method for imparting to hair finger combability and softness during rinsing and softness after towel drying, comprising applying the cleansing composition for skin or hair according to any one of the aforementioned [1] to [27] to hair.

[31] A method for imparting moist feeling to skin, comprising applying the cleansing composition for skin or hair according to any one of the aforementioned [1] to [27] to skin.

[32] The cleansing composition for skin or hair according to any one of the aforementioned [1] to [27] for washing hair.

[33] The cleansing composition for skin or hair according to any one of the aforementioned [1] to [27] for washing skin.

[34] Use of the cleansing composition for skin or hair according to any one of the aforementioned [1] to [27] for washing hair.

[35] Use of the cleansing composition for skin or hair according to any one of the aforementioned [1] to [27] for washing skin.

[36] The cleansing composition for skin or hair according to any one of the aforementioned [1] to [27] for imparting to hair finger combability and softness during rinsing and softness after towel drying.

[37] The cleansing composition for skin or hair according to any one of the aforementioned [1] to [27] for imparting moist feeling to skin.

[38] Use of the cleansing composition for skin or hair according to any one of the aforementioned [1] to [27] for imparting to hair finger combability and softness during rinsing and softness after towel drying.

[39] Use of the cleansing composition for skin or hair according to any one of the aforementioned [1] to [27] for imparting moist feeling to skin.

[40] The cleansing composition for skin or hair according to any one of the aforementioned [1] to [27] for improving foam durability.

[41] The cleansing composition for skin or hair according to any one of the aforementioned [1] to [27] for improving rinse feel.

EXAMPLES

Hereinbelow, the present invention will be specifically described with reference to Examples. It should be noted that unless otherwise specifically noted, "part" means "part by mass" and "%" means "% by mass" in the following Examples and Comparative Examples. Also, the methods used for measuring various physical property are as follows.

(1) Conditions of Measurement (i) Method for Measuring the Position of a Double Bond in the Raw Material Internal Olefin The position of a double bond in a raw material internal olefin was measured by gas chromatography (hereinbelow, abbreviated as GC). Specifically, an internal olefin was converted to a dithiated derivative by reaction with dimethyl disulfide, and each component was separated by GC. As a result, the position of a double bond in an internal olefin was found based on the peak area of each component.

The apparatus and analytical conditions used for the measurement are as follows. GC apparatus (trade name: HP6890, the product of Hewlett-Packard Company); Column (trade name: Ultra-Alloy-1HT capillary column, 30 m×250 μm×0.15 μm, the product of Frontier Laboratories Ltd.); Detector (flame ionization detector (FID)); Injection temperature of 300° C.; Detector temperature of 350° C.; and He flow rate of 4.6 mL/minute.

(ii) Method for Measuring the Mass Ratio of Hydroxy Form/Olefin Form

The mass ratio of hydroxy form/olefin form of the internal olefin sulfonate was measured by HPLC-MS. Specifically, the hydroxy form and the olefin form were separated by HPLC and each form was identified by separately analyzing with MS. As a result, from the resulting HPLC-MS peak area, the fraction of each form was obtained.

The apparatus and analytical conditions used for the measurement are as follows. HPLC apparatus (trade name: Agilent technology 1100, the product of Agilent Technologies, Inc.); Column (trade name: L-column ODS 4.6×150 mm, the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 minute (A/B=30/70%)→10 minutes (30/70%)→55 minutes (0/100%)→65 minutes (0/100%)→66 minutes (30/70%)→75 minutes (30/70%)); MS apparatus (trade name: Agilent technology 1100 MS SL (G1946D)); and MS detection (anion detection m/z 60-1600, UV 240 nm)

(iii) Method for Measuring the Content of the Raw Material Internal Olefin

The content of the raw material internal olefin of the internal olefin sulfonate was measured by GC. Specifically, ethanol and petroleum ether were added to an aqueous solution of internal olefin sulfonate, followed by extraction to give olefin in the petroleum ether phase. As a result, from the GC peak area of the olefin, the amount thereof was quantitated. The apparatus and analytical conditions used for the measurement are as follows. GC apparatus (trade name: Agilent technology 6850, the product of Agilent Technologies, Inc.); Column (trade name: Ultra-Alloy-1HT capillary column, 15 m×250 μm×0.15 μm, the product of Frontier Laboratories, Ltd.); Detector (flame ionization detector (FID)); Injection temperature of 300° C.; Detector temperature of 350° C.; and He flow rate of 3.8 mL/minute.

(iv) Method for Measuring the Content of Inorganic Compounds

The content of inorganic compounds was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(v) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. As a result, from the GC peak area of the paraffin, the amount thereof was quantitated. It should be noted that the apparatus and analytical conditions used for measurement are the same as those used for the measurement of the content of the raw material internal olefin.

(vi) Method for Measuring the Content of Internal Olefin Sulfonate in which a Sulfonate Group is Present at a C-2 Position The linkage position of the sulfonate group was measured by GC. Specifically, the resulting internal olefin sulfonate (A) was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus (trade name: Agilent technology 6850, the product of Agilent Technologies, Inc.); Column (trade name: HP-1 capillary column, 30 m×320 μm×0.25 the product of Agilent Technologies, Inc.); Detector (hydrogen flame ionization detector (FID)); Injection temperature of 300° C.; Detector temperature of 300° C.; He flow rate of 1.0 mL/min.; oven (60° C. (0 min.)→10° C./min.→300° C. (10 min.)).

(2) Production of an Internal Olefin

Production Example A

Into a flask with a stirrer, 7000 g (25.9 moles) of 1-octadecanol (trade name: KALCOL 8098, the product of Kao Corporation), and as a solid acid catalyst, 1050 g (15 wt % relative to the raw material alcohol) of γ-alumina (STREM Chemicals, Inc.) were placed, and reactions were allowed to proceed for 13 hours at 285° C. while stirring and passing nitrogen (7000 mL/minute) through the system. The alcohol conversion ratio was 100% and the purity of C18 internal olefin was 98.5% after the completion of the reaction. The resulting crude internal olefin was transferred to a distillation flask and distilled at from 148 to 158° C./0.5 mmHg, whereby 100% pure internal olefin having 18 carbon atoms was obtained. The double bond distribution in the resulting internal olefin was 0.7% by mass at C-1 position, 16.9% by mass at C-2 position, 15.9% by mass at C-3 position, 16.0% by mass at C-4 position, 14.7% by mass at C-5 position, 11.2% by mass at C-6 position, 10.2% by mass at C-7 position, and 14.6% by mass in total at C-8 and 9 positions.

Production Example B

Into a flask with a stirrer, 7000 g (28.9 moles) of 1-hexadecanol (trade name: KALCOL 6098, the product of Kao Corporation), and as a solid acid catalyst, 700 g (10% by mass relative to the raw material alcohol) of γ-alumina (STREM Chemicals, Inc.) were placed, and reactions were allowed to proceed for five hours at 280° C. while stirring and passing nitrogen (7000 mL/minute) through the system. The alcohol conversion ratio was 100%, and the purity of C16 internal, olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.5% by mass at C-1 position, 16.5% by mass at C-2 position, 15.4% by mass at C-3 position, 16.4% by mass at C-4 position, 17.2% by mass at C-5 position, 14.2% by mass at C-6 position, and 19.8% by mass in total at C-7 and 8 positions.

Production Example C

Into a flask with a stirrer, 7000 g (28.9 moles) of 1-hexadecanol (trade name: KALCOL 6098, the product of Kao Corporation), and as a solid acid catalyst, 700 g (10 wt % relative to the raw material alcohol) of γ-alumina (STREM Chemicals, Inc.) were placed, and reactions were allowed to proceed for three hours at 280° C. while stirring and passing nitrogen (7000 mL/minute) through the system. The alcohol conversion ratio was 100%, and the purity of C16 internal olefin was 99.6% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 1.8% by mass at C-1 position, 30.4% by mass at C-2 position, 23.9% by mass at C-3 position, 16.8% by mass at C-4 position, 12.0% by mass at C-5 position, 7.4% by mass at C-6 position, and 7.8% by mass in total at C-7 and 8 positions.

Production Example D

Into a flask with a stirrer, 7000 g (25.9 moles) of 1-octadecanol (trade name: KALCOL 8098, the product of Kao Corporation), and as a solid acid catalyst, 700 g (10 wt % relative to the raw material alcohol) of γ-alumina (STREM Chemicals, Inc.) were placed, and reactions were allowed to proceed for 10 hours at 280° C. while stirring and passing nitrogen (7000 mL/minute) through the system. The alcohol conversion ratio was 100%, and the purity of C18 internal olefin was 98.2% after the completion of the reaction. The resulting crude internal olefin was transferred to a distillation flask and distilled at the temperature inside of from 148 to 158° C./0.5 mmHg, whereby 100% pure purified internal olefin having 18 carbon atoms was obtained. The double bond distribution in the resulting internal olefin was 0.8% by mass at C-1 position, 31.3% by mass at C-2 position, 22.9% by mass at C-3 position, 15.5% by mass at C-4 position, 10.8% by mass at C-5 position, 7.2% by mass at C-6 position, 5.3% by mass at C-7 position, and 6.2% by mass in total at C-8 and 9 positions.

Production Example E

A reaction time was adjusted in a same manner as Production Example C, in order to produce C16 internal olefin having 100% of purity. The double bond distribution of the resulting internal olefin was 0.8% by mass at a C-1 position, 26.8% by mass at a C-2 position, 22.6% by mass at a C-3 position, 18.2% by mass at a C-4 position, 16.5% by mass at a C-5 position, 8.5% by mass at a C-6 position, and 6.6% by mass in total at C-7 and C-8 positions.

Production Example F

A reaction time was adjusted in a same manner as Production Example D, in order to produce C18 internal olefin having 100% of purity. The double bond distribution of the resulting internal olefin was 0.3% by mass at a C-1 position, 19.0% by mass at a C-2 position, 17.6% by mass at a C-3 position, 17.4% by mass at a C-4 position, 14.9% by mass at a C-5 position, 12.3% by mass at a C-6 position, 8.8% by mass at a C-7 position, and 9.8% by mass in total at C-8 and C-9 positions.

Production Example G 11.9 kg of the C16 internal olefin obtained in the Production Example E and 3.1 kg of the C18 internal olefin obtained in Production Example F were mixed to produce 15.0 kg of C16/C18 (mass ratio of 79.4/20.6) internal olefin. The double bond distribution of the resulting internal olefin was 0.7% by mass at a C-1 position, 25.2% by mass at a C-2 position, 21.6% by mass at a C-3 position, 18.0% by mass at a C-4 position, 16.2% by mass at a C-5 position, 9.3% by mass at a C-6 position, 4.4% by mass at a C-7 position, 3.6% by mass at a C-8 position, and 1.0% by mass at a C-9 position.

Production Example H

A reaction time was adjusted in a same manner as Production Example C, in order to produce C16 internal olefin having 100% of purity. The double bond distribution of the resulting internal olefin was 0.5% by mass at a C-1 position, 30.1% by mass at a C-2 position, 25.5% by mass at a C-3 position, 18.9% by mass at a C-4 position, 11.1% by mass at a C-5 position, 7.0% by mass at a C-6 position, and 7.0% by mass in total at C-7 and C-8 positions.

Production Example I

A reaction time was adjusted in a same manner as Production Example D, in order to produce C18 internal olefin having 100% of purity. The double bond distribution of the resulting internal olefin was 0.5% by mass at a C-1 position, 25.0% by mass at a C-2 position, 22.8% by mass at a C-3 position, 19.1% by mass at a C-4 position, 14.0% by mass at a C-5 position, 7.4% by mass at a C-6 position, 5.4% by mass at a C-7 position, and 5.8% by mass in total at C-8 and C-9 positions.

Production Example J

Into a flask with a stirrer, 6000 g (30.6 moles) of 1-tetradecene (trade name: LINEALENE 14, the product of Idemitsu Kosan Co., Ltd.), and as a solid acid catalyst, 173 g (2.9 wt % relative to the raw material 1-tetradecene) of β-zeolite (Zeolyst International, Inc.) were placed, and reactions were allowed to proceed for 21 hours at 120° C. while stirring and passing nitrogen (200 mL/minute) through the system. The internal isomerization ratio of α-olefin was 99.0%, and the purity of C14 internal olefin was 91.1% after the completion of the reaction. The resulting crude internal olefin was transferred to a distillation flask and distilled at from 130 to 136° C./from 12.8 to 13.5 mmHg, whereby 100% pure internal olefin having 14 carbon atoms was obtained. The double bond distribution of the resulting internal olefin was 1.3% by mass at C-1 position, 31.8% by mass at C-2 position, 23.8% by mass at C-3 position, 21.0% by mass at C-4 position, 8.6% by mass at C-5 position, and 13.6% by mass in total at C-6 and C-7 positions.

Production Example K

Into a flask with a stirrer, 6000 g (35.6 moles) of 1-dodecene (trade name: LINEALENE 12, the product of Idemitsu Kosan Co., Ltd.), and as a solid acid catalyst, 180 g (3.0 wt % relative to the raw material 1-dodecene) of β-zeolite (Zeolyst International, Inc.) were placed, and reactions were allowed to proceed for 12.5 hours at 120° C. while stirring and passing nitrogen (200 mL/minute) through the system. The internal isomerization ratio of α-olefin was 98.4%, and the purity of C12 internal olefin was 92.1% after the completion of the reaction. The resulting crude internal olefin was transferred to a distillation flask and distilled at from 134 to 138° C./from 75.0 to 78.8 mmHg, whereby 100% pure internal olefin having 12 carbon atoms was obtained. The double bond distribution of the resulting internal olefin was 0.5% by mass at C-1 position, 33.1% by mass at C-2 position, 23.7% by mass at C-3 position, 21.2% by mass at C-4 position, 15.0% by mass at C-5 position, and 6.8% by mass at C-6 position.

(3) Production of an Internal Olefin Sulfonate

Production Example 1

Using a thin film sulfonation reactor (14 mm in inner diameter and 4 m in length), the sulfonation reaction of the internal olefin having 16 carbon atoms produced in Production Example C was carried out by passing through sulfur trioxide gas containing a concentration of $SO_3$ at 2.8% by volume, while passing cooling water of 20° C. through the outer jacket of the reactor. It should be noted that the reaction molar ratio of $SO_3$/internal olefin was set at 1.09.

The resulting sulfonation product was added to an alkaline aqueous solution containing 1.2 times the molar amount of sodium hydroxide relative to the theoretical acid value (AV), followed by neutralization at 30° C. for one hour while stirring. The resulting neutralized product was hydrolyzed by heating at 160° C. for one hour in an autoclave, whereby a crude product of sodium C16 internal olefin sulfonate was obtained.

Then, 300 g of the crude product thus obtained was transferred to a separatory funnel, to which 300 mL of ethanol was added. Then, 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above operation was repeated three times. Then, the aqueous phase side was evaporated to dryness, whereby sodium internal olefin sulfonate (1) having 16 carbon atoms was obtained. The content of the raw material internal olefin was less than 100 ppm (below the GC detection limit) and that of inorganic compounds was 1.9% by mass. The above results are shown in Table 1.

Production Example 2

Except for using the internal olefin having 18 carbon atoms produced in Production Example D, sodium internal olefin sulfonate (2) having 18 carbon atoms was obtained under the same conditions as those used in Production Example 1. The content of the raw material internal olefin was less than 100 ppm (below the GC detection limit) and that of inorganic compounds was 0.9% by mass. The above results are shown in Table 1.

Production Example 3

Except for using the internal olefin having 16 carbon atoms produced in Production Example B, sodium internal olefin sulfonate having (3) 16 carbon atoms was obtained under the same conditions as those used in Production Example 1. The content of the raw material internal olefin was less than 100 ppm (below the GC detection limit) and that of inorganic compounds was 1.3% by mass. The above results are shown in Table 1.

Production Example 4

Except for using the internal olefin having 18 carbon atoms produced in Production Example A, sodium internal olefin sulfonate having (4) 18 carbon atoms was obtained under the same conditions as those used in Production Example 1. The content of the raw material internal olefin was less than 100 ppm (below the GC detection limit) and that of inorganic compounds was 1.7% by mass. The above results are shown in Table 1.

Production Example 5

The C16/18 internal olefin (the content of internal olefin in which double bonds are present at C-2 position is 25.2% by mass) produced in Production Example G was used as a raw material, and a sodium C16/C18 internal olefin sulfonate (5) was obtained by the same manner as in Production Example 1. The mass ratio of hydroxy form (sodium hydroxyalkane sulfonate)/olefin form (sodium olefin sulfonate) in the obtained sodium internal olefin sulfonate was 87/13. Also, the content of the raw material internal olefin contained in the obtained sodium internal olefin sulfonate was less than 100 ppm (below the GC detection limit) and that of inorganic compounds was 0.5% by mass.

Production Example 6

Except for using the internal olefin having 16 carbon atoms produced in Production Example H, sodium internal olefin sulfonate (6) having 16 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

Production Example 7

Except for using the internal olefin having 18 carbon atoms produced in Production Example I, sodium internal olefin sulfonate (7) having 18 carbon atoms was obtained under the same conditions as those used in Production Example 1. The content of the raw material internal olefin was less than 100 ppm (below the GC detection limit) and that of inorganic compounds was 0.1% by mass. The above results are shown in Table 1.

Production Example 8

Except for using the internal olefin having 14 carbon atoms produced in Production Example J, sodium internal olefin sulfonate (8) having 14 carbon atoms was obtained under the same conditions as those used in Production Example 1. The content of the raw material internal olefin was less than 100 ppm (below the GC detection limit) and that of inorganic compounds was 0.5% by mass. The above results are shown in Table 1.

Production Example 9

Except for using the internal olefin having 12 carbon atoms produced in Production Example K, sodium internal olefin sulfonate (9) having 12 carbon atoms was obtained under the same conditions as those used in Production Example 1. The content of the raw material internal olefin was less than 100 ppm (below the GC detection limit) and that of inorganic compounds was 0.2% by mass. The above results are shown in Table 1.

TABLE 1

| | Raw material internal olefin | | Internal olefin sulfonate | |
|---|---|---|---|---|
| | Number of carbon atoms | C-2 Double bond (%) | HAS/IOS (Mass ratio) | Content of internal olefin sulfonate in which sulfonate group is present at C-2 position (%) |
| Internal olefin sulfonate (1) | C16 | 30.4 | 80/20 | 20.3 |
| Internal olefin sulfonate (2) | C18 | 31.3 | 80/20 | 21.4 |
| Internal olefin sulfonate (3) | C16 | 16.5 | 80/20 | 9.3 |
| Internal olefin sulfonate (4) | C18 | 16.9 | 80/20 | 9.6 |
| Internal olefin sulfonate (5) | C16/C18 | 25.2 | 87/13 | 17.6 |
| Internal olefin sulfonate (6) | C16 | 30.1 | 80/20 | 19.9 |
| Internal olefin sulfonate (7) | C18 | 25.0 | 80/20 | 15.0 |
| Internal olefin sulfonate (8) | C14 | 31.8 | 92.8/7.4 | 22.0 |
| Internal olefin sulfonate (9) | C12 | 33.1 | 80/20 | 21.0 |

(4) Preparation of the Cleansing Compositions

Using sodium internal olefin sulfonates shown in Table 1, the cleansing compositions for hair or skin each having the compositions shown in from Tables 2 to 4 were prepared by a conventional method. Specifically, the component (B) was dissolved or homogeneously dispersed in water, and appropriate amounts of water and the component (A), and if necessary, the component (C) were placed in a beaker. The resulting mixture was heated to 60° C. and mixed, and then cooled to room temperature. Then, the mixture was supplemented with water and adjusted to pH 6 with a pH adjuster (a 50% aqueous solution of citric acid or a 10% aqueous solution of sodium hydroxide), whereby each cleansing composition was obtained.

It is to be noted that the cationized hydroxypropyl cellulose used in Example 15 was produced by successively performing the chipping process, cationization process, and hydroxypropylation process as shown below.

<Production of Cationized Hydroxypropyl Cellulose (C-HPC)>

[Chipping Process]

Wood pulp sheet (the product of Tembec Inc., Biofloc HV+, average degree of polymerization of 1770, degree of crystallinity of 74%, and water content of 7.0%) was processed by a sheet pelletizer (the product of HORAI Co, Ltd., “SGG-220”) into 3 to 5 mm square chip.

[Cationization Process]

In a mortar, 100 g of the pulp chips obtained by the aforementioned chipping process were mixed with 60.8 g of an aqueous solution of glycidyl trimethyl ammonium chloride (the product of Sakamoto Yakuhin Kogyo Co., Ltd., water content of 20%, purity of 90% or more), and the resulting mixture was put into a batch-type vibration mill (the product of Chuo Kakohki Co., Ltd., “MB-1”: total capacity of the container was 3.5 L, and 13 rods were made of SUS304 having circular cross sectional shape, each rod was 30 mm in diameter and 218 mm in length, at a filling rate of 57%), and pulverized for 12 minutes (vibration frequency of 20 Hz, amplitude of 8 mm, and a temperature of from 30 to 70° C.), whereby a powder mixture of cellulose and GMAC was obtained.

The resulting powder mixture was mixed with 14.8 g of a 48% aqueous solution of sodium hydroxide in a mortar, and then put into the aforementioned batch-type vibration mill. Pulverization was performed for 120 minutes under the same conditions, whereby cationized cellulose was obtained.

[Hydroxypropylation Process]

A kneader containing 100 g of cationized cellulose obtained after maturation (unneutralized, unpurified product) was heated to 70° C., to which 40.8 g of propylene oxide (the product of Kanto Chemical, Co., Inc., special grade reagent) was added dropwise while stirring and reactions were allowed to proceed for eight hours until propylene oxide was consumed and reflux was stopped.

Upon completion of the reaction, the mixture was removed from the kneader to give a light brown crude cationized hydroxypropyl cellulose powder. This crude cationized hydroxypropyl cellulose powder was collected and neutralized with acetic acid. In order to find out the degree of substitution of the propyleneoxy group and that of the cationized ethyleneoxy group, the neutralized product was purified using a dialysis membrane (a molecular weight cut off of 1000) and then the aqueous solution was freeze-dried, whereby purified C-HPC was obtained.

The degree of substitution of the cationized ethyleneoxy group and the degree of substitution of the propyleneoxy group in the purified cationized hydroxypropyl cellulose thus obtained were calculated as 0.22 and 1.1, respectively, in accordance with the following method. Also, the average degree of polymerization was measured as 539 in accordance with the following method.

<<Calculation of the Degree of Substitution in C-HPC>>

The C-HPC thus obtained was purified using a dialysis membrane (a molecular weight cutoff of 1000) and then the aqueous solution was freeze-dried, whereby purified C-HPC was obtained. The chlorine content (%) in the purified C-HPC thus obtained was measured by elementary analysis, and based on the approximation that the number of cationic groups contained in C-HPC and the number of chloride ions as the counter ions, were the same, the amount of cationized ethyleneoxy groups (—CH($Y^1$)—CH($Y^2$)O—) (a (mole/g)) contained in the unit mass of C-HPC was obtained from the following calculation formula.

$$a\text{(mole/g)}=\text{the chlorine content (\%) obtained by elementary analysis}/(35.5\times 100) \quad \text{(A)}$$

Except that the subject of analysis is the purified C-HPC but not hydroxypropyl cellulose, the content of hydroxypropoxy groups (%) was measured in accordance with the "method of analysis of hydroxypropyl cellulose" described in Japanese Pharmacopoeia. The content of hydroxypropoxy groups [formula weight ($OC_3H_6OH$=75.09)] (b mole/g) was obtained from the following calculation formula (B).

$$b\text{(mole/g)}=\text{the content of hydroxypropoxy groups (\%) obtained from gas chromatography}/(75.09\times 100) \quad \text{(B)}$$

From the resulting values of a and b and the following formulas (C) and (D), the degree of substitution of the cationized ethyleneoxy group (k) and the degree of substitution of the propyleneoxy group (m) were calculated.

$$a=k/(162+k\times K+m\times 58) \quad \text{(C)}$$

$$b=m/(162+k\times K+m\times 58) \quad \text{(D)}$$

wherein, k and K each represent the degree of substitution and the formula weight of the cationized ethyleneoxy group, and m represents the degree of substitution of the propyleneoxy group.

<<Measurement of the Average Degree of Polymerization (Cuprammonium Process)>>

Preparation of a solution for measurement Into a measuring flask (100 mL), 0.5 g of cuprous chloride and from 20 to 30 mL of 25% aqueous ammonia were added. After completely dissolving cuprous chloride, 1.0 g of cupric hydroxide and 25% aqueous ammonia were added to make up the volume to just below the marked line. The resulting mixture was stirred for from 30 to 40 minutes until complete dissolution. Subsequently, precisely weighed C-HPC was added and the flask was filled with the aforementioned aqueous ammonia up to the marked line. The flask was then hermetically sealed and stirred with a magnetic stirrer for 12 hours, whereby a solution for measurement was prepared. By varying the amount of cellulose added between 20 to 500 mg, solutions for measurement having various concentrations of cellulose were prepared.

The solutions for measurement thus obtained (cuprammonium solution) were put in an Ubbelohde viscometer, and left still in a constant temperature bath (20±0.1° C.) for one hour, and then the downflow rate of the solution was measured.

From the downflow time (t (second)) of the cuprammonium solutions having various concentrations of cellulose (g/dL) and the downflow time (t0 (second)) of an aqueous solution of cuprammonium without cellulose, the reduced viscosity at each concentration (ηsp/c) was obtained by the following formula (E).

$$\eta sp/c=\{(t-t0)/t0\}/c \quad \text{(E)}$$

(c: concentration in terms of cellulose (g/dL))

Here, the concentration in terms of cellulose (ccell) refers to the mass (g) of the cellulose framework contained per dL solution for measurement, which is defined by the following calculation formula (F).

$$c\text{cell}=u\times 162/(162+k\times K+m\times 58) \quad \text{(F)}$$

wherein, u refers to the mass (g) of the precisely weighed C-HPC used in the preparation of the solution for measurement, and k, K, and m each represent the same meaning as in the aforementioned calculation formulas (C) and (D).

Further, the intrinsic viscosity [η] (dL/g) was obtained by extrapolating the reduced viscosity back to c=0, and the viscosity-average degree of polymerization (DP) was obtained by the following formula (G).

$$\text{DP}=2000\times[\eta] \quad \text{(G)}$$

(5) Hair Evaluation after Washing

Each of the following components was placed in a beaker and heated to 80° C., followed by mixing. After confirming homogeneous dissolution, the mixture was cooled to give a plain shampoo. A hair bundle (Japanese hair which was not subjected to treatment such as bleaching and hair coloring, approximately 20 cm long, 15 g) was washed with the plain shampoo thus obtained, whereby a tress for evaluation was obtained.

(Composition of the Plain Shampoo)

| (Component) | (% by mass) |
|---|---|
| Sodium polyoxyethylene lauryl ether sulfate (42.0% as EMAL E-27C (the product of Kao Corporation, active content, 27% by mass)) | 11.3 |
| Coconut oil fatty acid N-methyl ethanolamide (AMINON C-11S (the product of Kao Corporation)) | 3.0 |
| Citric acid | 0.2 |
| Methylparaben | 0.3 |
| Purified water | Balance |
| Total | 100.0 |

The tress for evaluation thus obtained was washed with each cleansing composition, and was evaluated for finger combability of the hair, softness of hair during rinsing, and softness of hair after towel drying after rinsing by five expert panelists based on the following evaluation criteria and evaluation method.

Also, in order to evaluate a foam retention (durability) in the presence of an oily component such as stain of sebum, 0.05 ml of model sebum was applied to the hair, and was washed. Then, foam durability during washing was evaluated. The model sebum was prepared by uniformly mixing 4/1% by mass of triolein/lanolin at 40° C.

The results are shown in Tables 2 and 3.

(Evaluation Criteria and Evaluation Method)

Finger combability of the hair during rinsing

5: Excellent finger combability
4: Good finger combability
3: Fair (equivalent to Comparative Example 1)
2: Poor finger combability
1: Very poor finger combability Softness of the Hair During Rinsing 5: Very soft
4: Soft
3: Fair (equivalent to Comparative Example 1)
2: Hard
1: Very hard Softness after Towel Drying 5: Very soft
4: Soft
3: Fair (equivalent to Comparative Example 1)
2: Hard
1: Very hard Foam Durability 5: Foam durability is very good (not feeling a decrease in the volume of foam during washing)
4: Foam durability is good (less decrease in the volume of foam)
3: Ordinary foam durability (equivalent to Comparative Example 1)
2: Foam durability was poor (remarkable decrease in the volume of foam)
1: Foam was not maintained (defoaming was found during washing)

TABLE 2

| | Cleansing composition for hair (shampoo) | | Examples 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| Formulation (part by mass) | (A) | Internal olefin sulfonate (1) | 12.0 | | | | | | | | | | | | | | |
| | | Internal olefin sulfonate (2) | | 12.0 | | | | | | | | | | | | | |
| | | Internal olefin sulfonate (3) | | | 12.0 | | 9.6 | 9.0 | 7.2 | 15.0 | 4.0 | 9.6 | 9.6 | | | | |
| | | Internal olefin sulfonate (4) | | | | 12.0 | 2.4 | 3.0 | 4.8 | 5.0 | 1.0 | 2.4 | 2.4 | | | | |
| | | Internal olefin sulfonate (5) | | | | | | | | | | | | 12.0 | | | |
| | | Internal olefin sulfonate (6) | | | | | | | | | | | | | 12.0 | | 9.6 |
| | | Internal olefin sulfonate (7) | | | | | | | | | | | | | | 12.0 | 2.4 |
| | | Internal olefin sulfonate (8) | | | | | | | | | | | | | | | |
| | | Internal olefin sulfonate (9) | | | | | | | | | | | | | | | |
| | | Sodium lauryl ether sulfate *1 | | | | | | | | | | | | | | | |
| | | Sodium lauryl sulfate *2 | | | | | | | | | | | | | | | |
| | | Sodium α-olefin sulfonate *3 | | | | | | | | | | | | | | | |
| | | Secondary alkane sulfonate *4 | | | | | | | | | | | | | | | |
| | | Sodium lauryl ether acetate *5 | | | | | | | | | | | | | | | |
| | (B) | Cationized guar gum *6 | 0.3 | 0.3 | 0.3 | 0.3 | 0.3 | 0.3 | 0.3 | 0.3 | 0.3 | 1.0 | 0.1 | 0.3 | 0.3 | 0.3 | 0.3 |
| | | pH Adjuster | q.s. | | | | | | | | | | | | | | |
| | | Purified water | Balance | | | | | | | | | | | | | | |
| | Content of internal olefin in which double bond is present at C-2 | | 30.4 | 31.3 | 16.5 | 16.9 | 16.6 | 16.6 | 16.7 | 16.6 | 16.6 | 16.6 | 16.6 | 25 | 30.1 | 25.0 | 29.1 |

TABLE 2-continued

| | | | | | | | | | | | | | | | | |
|---|---|---|---|---|---|---|---|---|---|---|---|---|---|---|---|---|
| | position in raw material internal olefin (% by mass) | | | | | | | | | | | | | | | |
| | C16/C18 Content in component (A) (% by mass) | 100 | 100 | 100 | 100 | 100 | 100 | 100 | 100 | 100 | 100 | 100 | 100 | 100 | 100 | 100 |
| | Content of internal olefin sulfonate in which sulfonate group is present at C-2 position (% by mass) | 20.3 | 21.4 | 9.3 | 9.6 | 9.4 | 9.4 | 9.4 | 9.4 | 9.4 | 9.4 | 9.4 | 17.6 | 19.9 | 15 | 18.9 |
| Evaluation results | Finger combability during rinsing | 3.6 | 4.8 | 3.6 | 4.8 | 4.6 | 4.6 | 4.6 | 4.4 | 4.4 | 4.8 | 4.2 | 4.2 | 4.0 | 4.2 | 4.2 |
| | Softness during rinsing | 4.2 | 4.4 | 4.6 | 4.8 | 4.8 | 4.8 | 4.8 | 4.8 | 4.4 | 4.8 | 4.2 | 5.0 | 4.0 | 5.0 | 5.0 |
| | Softness after towel drying | 4.4 | 3.2 | 4.8 | 3.6 | 4.6 | 4.4 | 4.0 | 4.6 | 4.4 | 4.0 | 4.4 | 4.6 | 4.2 | 4.8 | 4.6 |
| | Durability of foam | — | — | — | — | 4.0 | — | — | — | — | — | — | 5.0 | 4.2 | 4.0 | 5.0 |

| Cleansing composition for hair (shampoo) | | | Examples | | | | | | | | | | Comparative Examples | | | | |
|---|---|---|---|---|---|---|---|---|---|---|---|---|---|---|---|---|---|
| | | | 16 | 17 | 18 | 19 | 20 | 21 | 22 | 23 | 24 | 25 | 1 | 2 | 3 | 4 | 5 |
| Formulation (part by mass) | (A) | Internal olefin sulfonate (1) | | | | | | | | | | | | | | | |
| | | Internal olefin sulfonate (2) | | | | | | | | | | | | | | | |
| | | Internal olefin sulfonate (3) | | | | | | | | | | | | | | | |
| | | Internal olefin sulfonate (4) | | | | | | | | | | | | | | | |
| | | Internal olefin sulfonate (5) | | | | | | | | | | | | | | | |
| | | Internal olefin sulfonate (6) | 9.0 | 7.2 | 15.0 | 4.0 | 9.6 | 9.6 | 4.8 | 2.9 | | | | | | | |
| | | Internal olefin sulfonate (7) | 3.0 | 4.8 | 5.0 | 1.0 | 2.4 | 2.4 | 1.2 | 0.7 | | | | | | | |
| | | Internal olefin sulfonate (8) | | | | | | | 6.0 | 8.4 | 12.0 | | | | | | |
| | | Internal olefin sulfonate (9) | | | | | | | | | | 12.0 | | | | | |
| | | Sodium lauryl ether sulfate *1 | | | | | | | | | | | 12.0 | | | | |
| | | Sodium lauryl sulfate *2 | | | | | | | | | | | | 12.0 | | | |
| | | Sodium α-olefin sulfonate *3 | | | | | | | | | | | | | 12.0 | | |
| | | Secondary alkane sulfonate *4 | | | | | | | | | | | | | | 12.0 | |
| | | Sodium lauryl ether acetate *5 | | | | | | | | | | | | | | | 12.0 |
| | (B) | Cationized guar gum *6 | 0.3 | 0.3 | 0.3 | 0.3 | 1.0 | 0.1 | 0.3 | 0.3 | 0.3 | 0.3 | 0.3 | 0.3 | 0.3 | 0.3 | 0.3 |
| | | pH Adjuster | | | | | | | | q.s. | | | | | | | |
| | | Purified water | | | | | | | | Balance | | | | | | | |
| | Content of internal olefin in which double bond is present at C-2 position in raw material internal olefin (% by mass) | | 28.8 | 28.1 | 28.8 | 29.1 | 29.1 | 29.1 | 30.4 | 31.0 | 31.8 | 33.1 | | | | | |
| | C16/C18 Content in component (A) (% by mass) | | 100 | 100 | 100 | 100 | 100 | 100 | 50 | 30 | 0 | 0 | | | | | |
| | Content of internal olefin sulfonate in which sulfonate group is present at C-2 position (% by mass) | | 18.7 | 17.9 | 18.7 | 18.9 | 18.9 | 18.9 | 20.5 | 21.1 | 22 | 21 | | | | | |
| Evaluation results | | Finger combability during rinsing | 4.2 | 4.2 | 4.0 | 4.2 | 4.8 | 4.0 | 4.0 | 3.8 | 3.8 | 3.6 | 3.0 | 2.6 | 2.0 | 2.6 | 3.6 |
| | | Softness during rinsing | 5.0 | 5.0 | 4.6 | 4.8 | 4.8 | 5.0 | 5.0 | 5.0 | 5.0 | 5.0 | 3.0 | 3.0 | 2.4 | 3.8 | 3.0 |
| | | Softness after towel drying | 4.6 | 4.6 | 4.2 | 4.6 | 4.8 | 4.6 | 4.6 | 4.6 | 4.8 | 4.8 | 3.0 | 3.0 | 2.6 | 3.6 | 3.0 |
| | | Durability of foam | 4.8 | 4.4 | 5.0 | 4.6 | 5.0 | 4.2 | 4.0 | 3.8 | 3.8 | 3.4 | 3.0 | — | — | — | — |

*1 The product of Kao Corporation, trade name: EMAL 270S (active ingredient, 70%) was added at 17.14%.
*2 The product of Kao Corporation, trade name: EMAL 30N-S
*3 The product of Lion Corporation, trade name: LJPOLAN LB-440 (active ingredient, 36%) was added at 33.33%.
*4 The product of LANXESS K.K., trade name: Mersolat (active ingredient 70%) was added at 17.14%.
*5 The product of Kao Corporation, trade name: KAO AKYPO RLM-45NV (active ingredient 23.5%) was added at 51.06%.
*6 The product of Rhodia: JAGUAR C-13S

TABLE 3

| Cleansing composition for hair (shampoo) | | | Examples 26 | 27 | 28 | 29 | 30 | 31 | 32 | 33 | 34 | 35 | 36 | 37 | 38 |
|---|---|---|---|---|---|---|---|---|---|---|---|---|---|---|---|
| For- | (A) | Internal olefin sulfonate (3) | 9.6 | 9.6 | 9.6 | 9.6 | 9.6 | 9.6 | 9.6 | 9.6 | 9.6 | 9.6 | 9.6 | 9.6 | 9.6 |
| mu- | | Internal olefin sulfonate (4) | 2.4 | 2.4 | 2.4 | 2.4 | 2.4 | 2.4 | 2.4 | 2.4 | 2.4 | 2.4 | 2.4 | 2.4 | 2.4 |
| la- | | Internal olefin sulfonate (6) | | | | | | | | | | | | | |
| tion | | Internal olefin sulfonate (7) | | | | | | | | | | | | | |
| (part | (B) | Cationized hydroxyethyl cellulose *1 | 0.3 | | | | | | | | | | | | |
| by | | Cationized hydroxyethyl cellulose *2 | | 0.3 | | | | | | | | | | | |
| mass) | | Cationized hydroxyethyl cellulose *3 | | | 0.3 | | | | | | | | | | |
| | | Cationized hydroxypropyl cellulos | | | | 0.3 | | | | | | | | | |
| | | Cationized guar gum *4 | | | | | 0.3 | | | | | | | | |
| | | *Caesalpinia spinosa* hydroxypropyltrimonium chloride *5 | | | | | | 0.3 | | | | | | | |
| | | *Cassia* hydroxypropyltrimonium chloride *6 | | | | | | | 0.3 | | | | | | |
| | | Polyquaternium-6 *7 | | | | | | | | 0.3 | | | | | |
| | | Polyquaternium-7 *8 | | | | | | | | | 0.3 | | | | |
| | | Polyquaternium-47 *9 | | | | | | | | | | 0.3 | | | |
| | | Polyquaternium-87 *10 | | | | | | | | | | | 0.3 | | |
| | | Polyquaternium-52 *11 | | | | | | | | | | | | 0.3 | |
| | | Polyquaternium-52 *12 | | | | | | | | | | | | | 0.3 |
| | | pH Adjuster | | | | | | | q.s. | | | | | | |
| | | Purified water | | | | | | | Balance | | | | | | |
| Evaluation results | | Finger combability during rinsing | 4.4 | 4.4 | 4.4 | 4.0 | 4.8 | 4.8 | 4.8 | 3.8 | 4.0 | 4.0 | 4.0 | 4.6 | 4.8 |
| | | Softness duringrinsing | 4.0 | 4.0 | 4.4 | 4.0 | 4.4 | 4.4 | 4.8 | 4.4 | 4.4 | 4.4 | 4.4 | 4.8 | 4.8 |
| | | Softness after towel drying | 4.8 | 4.8 | 4.8 | 4.4 | 4.8 | 4.8 | 4.8 | 4.8 | 4.8 | 4.8 | 4.8 | 4.6 | 4.6 |
| | | Durability of foam | — | — | — | — | — | — | — | — | — | — | — | — | — |

| Cleansing composition for hair (shampoo) | | | Examples 39 | 40 | 41 | 42 | 43 | 44 | 45 | 46 | 47 | 48 | 49 | 50 | 51 |
|---|---|---|---|---|---|---|---|---|---|---|---|---|---|---|---|
| For- | (A) | Internal olefin sulfonate (3) | | | | | | | | | | | | | |
| mu- | | Internal olefin sulfonate (4) | | | | | | | | | | | | | |
| la- | | Internal olefin sulfonate (6) | 9.6 | 9.6 | 9.6 | 9.6 | 9.6 | 9.6 | 9.6 | 9.6 | 9.6 | 9.6 | 9.6 | 9.6 | 9.6 |
| tion | | Internal olefin sulfonate (7) | 2.4 | 2.4 | 2.4 | 2.4 | 2.4 | 2.4 | 2.4 | 2.4 | 2.4 | 2.4 | 2.4 | 2.4 | 2.4 |
| (part | (B) | Cationized hydroxyethyl cellulose *1 | 0.3 | | | | | | | | | | | | |
| by | | Cationized hydroxyethyl cellulose *2 | | 0.3 | | | | | | | | | | | |
| mass) | | Cationized hydroxyethyl cellulose *3 | | | 0.3 | | | | | | | | | | |
| | | Cationized hydroxypropyl cellulos | | | | 0.3 | | | | | | | | | |
| | | Cationized guar gum *4 | | | | | 0.3 | | | | | | | | |
| | | *Caesalpinia spinosa* hydroxypropyltrimonium chloride *5 | | | | | | 0.3 | | | | | | | |
| | | *Cassia* hydroxypropyltrimonium chloride *6 | | | | | | | 0.3 | | | | | | |
| | | Polyquaternium-6 *7 | | | | | | | | 0.3 | | | | | |
| | | Polyquaternium-7 *8 | | | | | | | | | 0.3 | | | | |
| | | Polyquaternium-47 *9 | | | | | | | | | | 0.3 | | | |
| | | Polyquaternium-87 *10 | | | | | | | | | | | 0.3 | | |
| | | Polyquaternium-52 *11 | | | | | | | | | | | | 0.3 | |
| | | Polyquaternium-52 *12 | | | | | | | | | | | | | 0.3 |
| | | pH Adjuster | | | | | | | q.s. | | | | | | |
| | | Purified water | | | | | | | Balance | | | | | | |
| Evaluation results | | Finger combability during rinsing | 3.8 | 3.8 | 4.0 | 3.8 | 4.4 | 4.6 | 4.4 | 3.8 | 4.2 | 4.0 | 3.8 | 4.4 | 4.8 |
| | | Softness during rinsing | 4.0 | 4.2 | 4.4 | 4.0 | 4.2 | 4.2 | 4.4 | 4.4 | 4.4 | 4.4 | 4.4 | 4.8 | 4.8 |
| | | Softness after towel drying | 4.4 | 4.6 | 4.8 | 4.4 | 4.8 | 4.8 | 4.6 | 4.8 | 4.8 | 4.6 | 4.6 | 4.8 | 4.8 |
| | | Durability of foam | 4.0 | 4.2 | 4.8 | 5.0 | 5.0 | 4.4 | 4.4 | 3.8 | 4.6 | 4.2 | 4.8 | 5.0 | 4.2 |

*1 The product of The Dow Chemical Company: UCARE JR400
*2 The product of Kao Corporation: trade name: POIZ C-80M
*3 The product of The Dow Chemical Company: UCARE JR30M
*4 The product of Rhodia: JAGUAR C-17
*5 The product of Toho Chemical Industry Co., Ltd.: CATINAL CTR-100
*6 The product of The Lubrizol Corporation: SensomerTM CT-250 polymer
*7 The product of The Lubrizol Corporation: Merquat 100
*8 The product of The Lubrizol Corporation: Merquat 550
*9 The product of The Lubrizol Corporation: Merquat 2001
*10 The product of BASF: Luviquat Sensation
*11 The product of Kao Corporation: SOFCARE KG-301W (active ingredient, 4%)
*12 The product of Kao Corporation: SOFCARE KG-101W (active ingredient, 4%)

(6) Skin Evaluation after Washing

Five expert panelists washed their hands with each cleansing composition, and evaluated the rinse feel after washing, the moist feeling to the skin after towel drying after rinsing, and durability of foam based on the following evaluation criteria and evaluation method. It should be noted that the durability of foam was evaluated based on the same criteria as those used for hair by applying model sebum to the hand.

The results are shown in Table 4.

Rinse Feel

5: Very good rinse feel
4: Good rinse feel
3: Fair rinse feel (equivalent to Comparative Example 1)
2: Poor rinse feel
1: Very poor rinse feel Moist Feeling 5: Very moist
4: Moist
3: Fair (equivalent to Comparative Example 1)
2: Not moist
1: Not moist at all and feels roughness

TABLE 4

| | | Cleansing composition for skin (body shampoo) | Examples 52 | 53 | 54 | 55 | 56 | 57 | 58 | 59 | 60 | 61 | 62 | 63 | 64 |
|---|---|---|---|---|---|---|---|---|---|---|---|---|---|---|---|
| Formulation (part by mass) | (A) | Internal olefin sulfonate (1) | 12.0 | | | | | | | | | | | | |
| | | Internal olefin sulfonate (2) | | 12.0 | | | | | | | | | | | |
| | | Internal olefin sulfonate (3) | | | 12.0 | | 9.6 | 9.0 | 7.2 | 15.0 | 4.0 | 9.6 | 9.6 | | |
| | | Internal olefin sulfonate (4) | | | | 12.0 | 2.4 | 3.0 | 4.8 | 5.0 | 1.0 | 2.4 | 2.4 | | |
| | | Internal olefin sulfonate (5) | | | | | | | | | | | | 12.0 | |
| | | Internal olefin sulfonate (6) | | | | | | | | | | | | | 12.0 |
| | | Internal olefin sulfonate (7) | | | | | | | | | | | | | |
| | | Sodium lauryl ether sulfate *1 | | | | | | | | | | | | | |
| | | Sodium lauryl sulfate *2 | | | | | | | | | | | | | |
| | | Sodium α-olefin sulfonate *3 | | | | | | | | | | | | | |
| | | Secondary alkane sulfonate *4 | | | | | | | | | | | | | |
| | (B) | Cationized guar gum *5 | 0.3 | 0.3 | 0.3 | 0.3 | 0.3 | 0.3 | 0.3 | 0.3 | 0.3 | 1.0 | 0.05 | 0.3 | 0.3 |
| | | pH Adjuster | | | | | | | q.s. | | | | | | |
| | | Purified water | | | | | | | Balance | | | | | | |
| | Content of internal olefin in which double bond is present at C-2 position in raw material internal olefin (% by mass) | | 30.4 | 31.3 | 16.5 | 16.9 | 16.6 | 16.6 | 16.7 | 16.6 | 16.6 | 16.6 | 16.6 | 25.2 | 30.1 |
| | C16/C18 Content in component (A)(% by mass) | | 100 | 100 | 100 | 100 | 100 | 100 | 100 | 100 | 100 | 100 | 100 | 100 | 100 |
| | Content of internal olefin sulfonate in which sulfonate group is present at C-2 position (% by mass) | | 20.3 | 21.4 | 9.3 | 9.6 | 9.4 | 9.4 | 9.4 | 9.4 | 9.4 | 9.4 | 9.4 | 17.6 | 19.9 |
| Evaluation results | | Rinse feel | 4.6 | 3.6 | 4.6 | 3.6 | 4.6 | 4.6 | 4.2 | 4.6 | 4.4 | 4.0 | 4.4 | 4.6 | 4.6 |
| | | Moist feeling after towel drying | 3.6 | 4.4 | 3.8 | 4.8 | 4.6 | 4.6 | 4.6 | 4.6 | 4.4 | 4.8 | 4.6 | 4.6 | 3.8 |
| | | Durability of foam | — | — | — | — | 4.2 | — | — | — | — | — | — | 4.8 | 4.0 |

| | | Cleansing composition for skin (body shampoo) | Examples 65 | 66 | 67 | 68 | 69 | 70 | 71 | 72 | Comparative Examples 1 | 2 | 3 | 4 |
|---|---|---|---|---|---|---|---|---|---|---|---|---|---|---|
| Formulation (part by mass) | (A) | Internal olefin sulfonate (1) | | | | | | | | | | | | |
| | | Internal olefin sulfonate (2) | | | | | | | | | | | | |
| | | Internal olefin sulfonate (3) | | | | | | | | | | | | |
| | | Internal olefin sulfonate (4) | | | | | | | | | | | | |
| | | Internal olefin sulfonate (5) | | | | | | | | | | | | |
| | | Internal olefin sulfonate (6) | | 9.6 | 9.0 | 7.2 | 15.0 | 4.0 | 9.6 | 9.6 | | | | |

TABLE 4-continued

| | | | | | | | | | | | | | |
|---|---|---|---|---|---|---|---|---|---|---|---|---|---|
| | Internal olefin sulfonate (7) | 12.0 | 2.4 | 3.0 | 4.8 | 5.0 | 1.0 | 2.4 | 2.4 | | | | |
| | Sodium lauryl ether sulfate *1 | | | | | | | | | 12.0 | | | |
| | Sodium lauryl sulfate *2 | | | | | | | | | | 12.0 | | |
| | Sodium α-olefin sulfonate *3 | | | | | | | | | | | 12.0 | |
| | Secondary alkane sulfonate *4 | | | | | | | | | | | | 12.0 |
| (B) | Cationized guar gum *5 | 0.3 | 0.3 | 0.3 | 0.3 | 0.3 | 0.3 | 1.0 | 0.05 | 0.3 | 0.3 | 0.3 | 0.3 |
| | pH Adjuster | q.s. | | | | | | | | | | | |
| | Purified water | Balance | | | | | | | | | | | |
| Content of internal olefin in which double bond is present at C-2 position in raw material internal olefin (% by mass) | | 25.0 | 29.1 | 28.8 | 28.1 | 28.8 | 29.1 | 29.1 | 29.1 | | | | |
| C16/C18 Content in component (A)(% by mass) | | 100 | 100 | 100 | 100 | 100 | 100 | 100 | 100 | | | | |
| Content of internal olefin sulfonate in which sulfonate group is present at C-2 position (% by mass) | | 15 | 18.9 | 18.7 | 17.9 | 18.7 | 18.9 | 18.9 | 18.9 | | | | |
| Evaluation results | Rinse feel | 3.6 | 4.6 | 4.6 | 4.0 | 4.4 | 4.4 | 4.0 | 4.4 | 3.0 | 3.0 | 3.0 | 2.6 |
| | Moist feeling after towel drying | 4.8 | 4.6 | 4.6 | 4.6 | 4.6 | 4.4 | 4.6 | 4.6 | 3.0 | 2.2 | 2.6 | 3.0 |
| | Durability of foam | 3.6 | 4.8 | 4.8 | 4.4 | 4.8 | 4.0 | 5.0 | 4.2 | 3.0 | — | — | — |

*1 The product of Kao Corporation, trade name: EMAL 270S (active ingredient, 70%) was added at 17.14%

*2 The product of Kao Corporation, trade name: EMAL 30N-S

*3 The product of Lion Corporation, trade name: LIPOLAN LB-440 (active ingredient, 36%) was added at 33.33%.

*4 The product of LANXESS K.K., trade name: Mersolat (active ingredient, 70%) was added at 17.14%.

*5 The product of Rhodia: JAGUAR C-13S

Example 73 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 13.4 |
| Sodium internal olefin sulfonate (4) | 3.4 |
| Lauryl betaine *1 | 1.5 |
| Coconut oil fatty acid amidopropyl betaine *2 | 1.1 |
| Cationized guar gum *3 | 0.3 |
| Ethylene glycol distearate *4 | 1.7 |
| Methylparaben | 0.3 |
| Citric acid (in an amount to bring pH to 6.0) | q.s. |
| Fragrance | q.s. |
| Purified water | Balance |
| Total | 100.0 |

*1: The product of Kao Corporation, trade name AMPHITOL 20BS (act. 31%) (The above composition is shown in terms of lauryl betaine)

*2: The product of Kao Corporation, trade name AMPHITOL 55AB (act. 30%) (The above composition is shown in terms of coconut oil fatty acid amidopropyl betaine)

*3: The product of Rhodia: JAGUAR C-13S (act. 100%)

*4: The product of Kao Chemical Corporation Shanghai, trade name PEARL CONC. SA-M2 (act. 20%) (The above composition is shown in terms of ethylene glycol distearate)

Example 74 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 11.7 |
| Sodium internal olefin sulfonate (4) | 2.9 |
| Sodium cocoamphoacetate *1 | 2.0 |
| Lauramide MIPA *2 | 0.7 |
| Cationized guar gum *3 | 0.3 |
| Ethylene glycol distearate *4 | 1.7 |
| Methylparaben | 0.3 |
| Citric acid (in an amount to bring pH to 6.0) | q.s. |
| Fragrance | q.s. |
| Purified water | balance |
| Total | 100.0 |

*1: The product of Kao Corporation, trade name AMPHITOL 20YB (act. 40%) (The above composition is shown in terms of sodium cocoamphoacetate)

*2: The product of Kawaken Fine Chemicals Co., Ltd.: Amizol PLME-A (act. 100%)

*3: The product of Rhodia: JAGUAR C-13S (act. 100%)

*4: The product of Kao Chemical Corporation Shanghai, trade name PEARL CONC. SA-M2 (act. 20%) (The above composition is shown in terms of ethylene glycol distearate)

Example 75 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 8.8 |
| Sodium internal olefin sulfonate (4) | 2.2 |
| Coconut oil fatty acid amidopropyl betaine *1 | 4.0 |
| Lauramide MIPA *2 | 0.7 |
| Polyquaternium-10 *3 | 0.4 |

-continued

| (Component) | (% by mass) |
|---|---|
| Methylparaben | 0.3 |
| Citric acid (in an amount to bring pH to 6.0) | q.s. |
| Fragrance | q.s. |
| Purified water | Balance |
| Total | 100.0 |

*1: The product of Kao Corporation, trade name AMPHITOL 55AB (act. 30%) (The above composition is shown in terms of coconut oil fatty acid amidopropyl betaine)
*2: The product of Kawaken Fine Chemicals Co., Ltd.: Amizol PLME-A (act. 100%)
*3: The product of Kao Corporation, trade name Poiz C-80M (act. 100%)

Example 76 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 10.4 |
| Sodium internal olefin sulfonate (4) | 2.6 |
| Coconut oil fatty acid amidopropyl betaine *1 | 1.0 |
| Lauramide MIPA *2 | 0.3 |
| Cationized guar gum *3 | 0.3 |
| Ethylene glycol distearate *4 | 0.7 |
| Methylparaben | 0.3 |
| Citric acid (in an amount to bring pH to 6.0) | q.s. |
| Fragrance | q.s. |
| Purified water | Balance |
| Total | 100.0 |

*1: The product of Kao Corporation, trade name AMPHITOL 55AB (act. 30%) (The above composition is shown in terms of coconut oil fatty acid amidopropyl betaine)
*2: The product of Kawaken Fine Chemicals Co., Ltd.: Amizol PLME-A (act. 100%)
*3: The product of Rhodia: JAGUAR C-13S (act. 100%)
*4: The product of Kao Chemical Corporation Shanghai, trade name PEARL CONC. SA-M2 (act. 20%) (The above composition is shown in terms of ethylene glycol distearate)

Example 77 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 12.6 |
| Sodium internal olefin sulfonate (4) | 3.1 |
| Cocamide MEA *1 | 1.8 |
| Cationized guar gum *2 | 0.3 |
| Ethylene glycol distearate *3 | 1.4 |
| Methylparaben | 0.3 |
| Citric acid (in an amount to bring pH to 6.0) | q.s. |
| Fragrance | q.s. |
| Purified water | Balance |
| Total | 100.0 |

*1: The product of Kawaken Fine Chemicals Co., Ltd.: Amizol CME (act. 100%)
*2: The product of Rhodia: JAGUAR C-13S (act. 100%)
*3: The product of Kao Chemical Corporation Shanghai, trade name PEARL CONC. SA-M2 (act. 20%) (The above composition is shown in terms of ethylene glycol distearate)

Example 78 (Shampoo)

A shampoo having the following composition was produced by a conventional method, and was evaluated in a similar manner to Example 1. As a result, this shampoo had favorable cleansing property, rinse feel, and softness during rinsing and after towel drying.

| (Component) | (% by mass) |
|---|---|
| Sodium internal olefin sulfonate (3) | 13.4 |
| Sodium internal olefin sulfonate (4) | 3.4 |
| Lauryl betaine *1 | 1.5 |
| Coconut oil fatty acid amidopropyl betaine *2 | 1.1 |
| Cationized guar gum *3 | 0.3 |
| Dimethicone *4 | 3.6 |
| Ethylene glycol distearate *5 | 1.7 |
| Methylparaben | 0.3 |
| Citric acid (in an amount to bring pH to 6.0) | q.s. |
| Fragrance | q.s. |
| Purified water | Balance |
| Total | 100.0 |

*1: The product of Kao Corporation, trade name AMPHITOL 20BS (act. 31%) (The above composition is shown in terms of lauryl betaine)
*2: The product of Kao Corporation, trade name AMPHITOL 55AB (act. 30%) (The above composition is shown in terms of Coconut oil fatty acid amidopropyl betaine)
*3: The product of Rhodia: JAGUAR C-13S (act. 100%)
*4: The product of Dow Corning Toray Co., Ltd., Silicone BY22-050A (active content 55%) (The above composition is shown in terms of dimethicone)
*5: The product of Kao Chemical Corporation Shanghai, trade name PEARL CONC. SA-M2 (act. 20%) (The above composition is shown in terms of ethylene glycol distearate)

Example 79 (Body Shampoo)

A body shampoo having the following composition was produced by a conventional method.

Both hands were wetted with water, to which 0.5 mL of the body shampoo thus obtained was applied, followed by lathering. Subsequently, the hands were rinsed with running water for 10 seconds, and water droplets were wiped off with a towel, and the feel of the skin after drying was evaluated.

As a result, this body shampoo had a good rinse feel, and the skin after drying had an excellent moist feel.

| (Component) | (% by mass) |
|---|---|
| Lauric acid | 8.6 |
| Myristic acid | 8.4 |
| Palmitic acid | 2.5 |
| Sodium internal olefin sulfonate (3) | 3.0 |
| Glycerin | 1.9 |
| Propylene glycol | 1.2 |
| Coconut oil fatty acid amidopropyl betaine *1 | 0.9 |
| Cationized guar gum *2 | 0.3 |
| Potassium hydroxide (in an amount to bring pH to 9.6) | q.s. |
| Fragrance and preservative | q.s. |
| Purified water | Balance |
| Total | 100.0 |

*1: The product of Kao Corporation, trade name AMPHITOL 55AB
*2: The product of Rhodia: JAGUAR C-13S Example 80 (Body Shampoo)

A body shampoo having the following composition was produced by a conventional method, and was evaluated in a similar manner to Example 79. As a result, the skin dried after washing with this body shampoo had an excellent moist feel.

| (Component) | (% by mass) |
|---|---|
| Sodium internal olefin sulfonate (3) | 8.0 |
| Sodium internal olefin sulfonate (4) | 2.0 |
| Coconut oil fatty acid amidopropyl betaine *1 | 1.5 |
| Coconut oil fatty acid monoethanolamide | 1.0 |
| Glycerin | 2.0 |
| Sodium chloride | 1.0 |
| Cationized guar gum *2 | 0.3 |
| Fragrance and preservative | q.s. |
| Purified water | Balance |
| Total | 100.0 |

*1: The product of Kao Corporation, trade name AMPHITOL 55AB
*2: The product of Rhodia: JAGUAR C-13S

INDUSTRIAL APPLICABILITY

The cleansing composition of the present invention can be favorably used in the fields of hair shampoo, body shampoo, facial cleanser, makeup remover, and hand soap, and the like, and further, it is also favorably applicable to animals such as dogs and cats.

The invention claimed is:

1. A method for washing hair, comprising applying a cleansing composition for skin or hair to hair, followed by washing and then rinsing, wherein the cleansing composition for skin or hair, comprises the following components (A) and (B):

(A) an internal olefin sulfonate having 12 or more and 24 or less carbon atoms, wherein said internal olefin sulfonate of 12 to 24 carbon atoms has a total content of (i) an internal olefin sulfonate having 16 carbon atoms and (ii) an internal olefin sulfonate having 18 carbon atoms of 95% by mass or more, wherein the content of said internal olefin sulfonate of 12 to 24 carbon atoms in which a sulfonate group is present at a C-2 position is 5% to 25% by mass, and wherein the mass content ratio of the internal olefin sulfonate having 16 carbon atoms to the internal olefin sulfonate having 18 carbon atoms in the internal olefin sulfonate (A) of 12 to 24 carbon atoms is from 50/50 to 99/1, and (B) a cationic polymer or an amphoteric polymer.

2. The method for washing hair of claim 1, wherein the cleansing composition for skin or hair is applied to hair to impart to hair finger combability and softness during rinsing and softness after towel drying.

3. The method for washing hair of claim 1, wherein the component (B) is an amphoteric polymer containing a diallyl quaternary ammonium salt/acrylic acid copolymer, an acrylic acid/diallyl quaternary ammonium salt/acrylamide copolymer, or an acrylic acid/methacrylamidopropyl quaternary ammonium salt/alkyl acrylic acid ester copolymer.

4. The method for washing hair of claim 1, wherein the component (B) is a cationic polymer, and is one or two or more selected from cationic galactomannan, cationized hydroxyethyl cellulose, cationized hydroxypropyl cellulose, cationized starch, and a synthetic polymer synthesized by a radical polymerization.

5. The method for washing hair of claim 4, wherein the component (B) is cationic galactomannan.

6. The method for washing hair of claim 5, wherein the cationic galactomannan is cationized guar gum.

7. The method for washing hair of claim 4, wherein the component (B) is cationized hydroxyethyl cellulose.

8. The method for washing hair of claim 4, wherein the component (B) is cationized hydroxypropyl cellulose.

9. The method for washing hair of claim 4, wherein the component (B) is cationized starch.

10. The method for washing hair of claim 4, wherein the component (B) is the synthetic polymer, and which is selected from a methacryloxyalkyl quaternary ammonium salt/acrylamide copolymer, a diallyl quaternary ammonium salt/acrylamide copolymer, a diallyl quaternary ammonium salt/acrylic acid copolymer, a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, and a diallyl quaternary ammonium salt/vinylpyrrolidone/vinylimidazole copolymer.

11. The method for washing hair of claim 1, further comprising a surfactant (C) other than the internal olefin sulfonate (A).

12. The method for washing hair of claim 1, further comprising an oil solution (D).

13. The method for washing hair of claim 1, wherein the mass content ratio of the component (A) to the component (B) is from 5 to 250.

14. The method for washing hair of claim 12, wherein the mass content ratio of the component (A) to the component (D) is from 0.2 to 1000.

15. The method for washing hair of claim 1, wherein the content mass ratio of the internal olefin sulfonate having 16 carbon atoms to the internal olefin sulfonate having 18 carbon atoms in the internal olefin sulfonate (A) is from 70/30 to 90/10.

16. A method for washing a body, comprising applying a cleansing composition for skin or hair to a surface of skin, followed by washing and then rinsing, wherein the cleansing composition for skin or hair, comprises the following components (A) and (B):

(A) an internal olefin sulfonate having 12 or more and 24 or less carbon atoms, wherein said internal olefin sulfonate of 12 to 24 carbon atoms has a total content of (i) an internal olefin sulfonate having 16 carbon atoms and (ii) an internal olefin sulfonate having 18 carbon atoms of 95% by mass or more, wherein the content of said internal olefin sulfonate of 12 to 24 carbon atoms in which a sulfonate group is present at a C-2 position is 5% to 25% by mass, and wherein the mass content ratio of the internal olefin sulfonate having 16 carbon atoms to the internal olefin sulfonate having 18 carbon atoms in the internal olefin sulfonate (A) of 12 to 24 carbon atoms is from 50/50 to 99/1, and (B) a cationic polymer or an amphoteric polymer.

17. The method for washing a body of claim 16, wherein the cleansing composition for skin or hair is applied to a surface of skin to impart moist feeling to skin.

18. The method for washing a body of claim 16, wherein the component (B) is an amphoteric polymer containing a diallyl quaternary ammonium salt/acrylic acid copolymer, an acrylic acid/diallyl quaternary ammonium salt/acrylamide copolymer, or an acrylic acid/methacrylamidopropyl quaternary ammonium salt/alkyl acrylic acid ester copolymer.

19. The method for washing a body of claim 16, wherein the component (B) is a cationic polymer, and is one or two or more selected from cationic galactomannan, cationized hydroxyethyl cellulose, cationized hydroxypropyl cellulose, cationized starch, and a synthetic polymer synthesized by a radical polymerization.

20. The method for washing a body of claim 19, wherein the component (B) is cationic galactomannan.

21. The method for washing a body of claim 20, wherein the cationic galactomannan is cationized guar gum.

22. The method for washing a body of claim 19, wherein the component (B) is cationized hydroxyethyl cellulose.

23. The method for washing a body of claim 19, wherein the component (B) is the synthetic polymer, and which is selected from a methacryloxyalkyl quaternary ammonium salt/acrylamide copolymer, a diallyl quaternary ammonium salt/acrylamide copolymer, a diallyl quaternary ammonium salt/acrylic acid copolymer, a diallyl quaternary ammonium salt/acrylamide/acrylic acid copolymer, a methacrylamide alkyl quaternary ammonium salt/acrylic acid/acrylic acid ester copolymer, a methacrylamide alkyl quaternary ammonium salt/acrylic acid/acrylamide copolymer, and a diallyl quaternary ammonium salt/vinylpyrrolidone/vinylimidazole copolymer.

24. The method for washing a body of claim 16, further comprising a surfactant (C) other than the internal olefin sulfonate (A).

25. The method for washing a body of claim 16, further comprising an oil solution (D).

26. The method for washing a body of claim 16, wherein the mass content ratio of the component (A) to the component (B) is from 5 to 250.

27. The method for washing a body of claim 25, wherein the mass content ratio of the component (A) to the component (D) is from 0.2 to 1000.

28. The method for washing a body of claim 16, wherein the content mass ratio of the internal olefin sulfonate having 16 carbon atoms to the internal olefin sulfonate having 18 carbon atoms in the internal olefin sulfonate (A) is from 70/30 to 90/10.

* * * * *